(12) United States Patent
Fujita et al.

(10) Patent No.: US 9,901,264 B2
(45) Date of Patent: Feb. 27, 2018

(54) BLOOD PRESSURE INFORMATION MEASUREMENT DEVICE CUFF AND BLOOD PRESSURE INFORMATION MEASUREMENT DEVICE PROVIDED THEREWITH

(75) Inventors: Reiji Fujita, Kyoto (JP); Yoshihiko Sano, Kyoto (JP); Minoru Taniguchi, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 873 days.

(21) Appl. No.: 13/596,403

(22) Filed: Aug. 28, 2012

(65) Prior Publication Data

US 2012/0323129 A1   Dec. 20, 2012

Related U.S. Application Data

(63) Continuation of application No. PCT/JP2011/052391, filed on Feb. 4, 2011.

(30) Foreign Application Priority Data

Mar. 3, 2010   (JP) ................................ 2010-046717

(51) Int. Cl.
*A61B 5/02*       (2006.01)
*A61B 5/022*      (2006.01)

(52) U.S. Cl.
CPC ................. *A61B 5/02233* (2013.01)

(58) Field of Classification Search
CPC ............ A61B 5/02233; A61B 5/02141; A61B 17/135; Y10T 24/2708; Y10T 24/4764
(Continued)

(56) References Cited

U.S. PATENT DOCUMENTS

| 4,429,699 A | * | 2/1984 | Hatschek | ............ A61B 5/02208 600/494 |
| 6,352,074 B1 | * | 3/2002 | Okada | ...................... A61F 5/028 128/100.1 |
| 2006/0047206 A1 | * | 3/2006 | Sano et al. | ..................... 600/490 |

FOREIGN PATENT DOCUMENTS

| JP | 58-054928 A | 4/1983 |
| JP | 63-147434 A | 6/1988 |

(Continued)

OTHER PUBLICATIONS

International Search Report issued in corresponding International Application No. PCT/JP2011/052391 dated Mar. 15, 2011 and English translation thereof (4 pages)

(Continued)

*Primary Examiner* — Puya Agahi
(74) *Attorney, Agent, or Firm* — Osha Liang LLP

(57) ABSTRACT

A blood pressure information measurement device cuff includes a fluid bladder, an outer cover, a first loop-shaped ring, and a second loop-shaped ring. The first loop-shaped ring is provided closer to one end portion of the outer cover than the position where the fluid bladder is located, and has an insertion hole for passing through and bending back another end portion of the outer cover. The second loop-shaped ring is provided on a front surface of the outer cover, and has an insertion hole for passing through the other end portion of the outer cover that has been passed through the first loop-shaped ring. According to the blood pressure information measurement device cuff, it is possible to repeatedly recreate the same fitted state with ease when the cuff is fitted to a measurement area.

10 Claims, 14 Drawing Sheets

(58) Field of Classification Search
USPC .................................. 600/499; 606/201–203
See application file for complete search history.

(56) References Cited

FOREIGN PATENT DOCUMENTS

| JP | H05-39504 U | 5/1993 |
| JP | 10-033490 A | 2/1998 |
| JP | 2002-369803 A | 12/2002 |

OTHER PUBLICATIONS

Patent Abstracts of Japan, Publication No. 10-033490, Published on Feb. 10, 1998, 1 page.
Patent Abstracts of Japan, Publication No. 2002-369803, Published on Dec. 24, 2002, 1 page.

\* cited by examiner

BLOOD PRESSURE INFORMATION MEASUREMENT DEVICE CUFF AND BLOOD PRESSURE INFORMATION MEASUREMENT DEVICE PROVIDED THEREWITH

TECHNICAL FIELD

The present invention relates to blood pressure information measurement device cuffs that are used while being worn on a measurement area when measuring blood pressure information such as a blood pressure value, and to blood pressure information measurement devices provided with such cuffs.

BACKGROUND ART

Blood pressure information measurement devices obtain blood pressure information of a measurement subject. The blood pressure information obtained by such blood pressure information measurement devices includes various types of information related to the circulatory system, such as a systolic blood pressure value (a maximum blood pressure value), a diastolic blood pressure value (a minimum blood pressure value), an average blood pressure value, a sphygmogram, pulse, AI (Augmentation Index) value, and the like of the measurement subject, and so on. Stress on the heart, changes in the hardness of arteries, or the like can be understood based on this blood pressure information. A blood pressure information measurement device is used in the early detection, prevention, treatment, and so on of circulatory system conditions.

Generally speaking, a blood pressure information measurement device cuff (called simply a "cuff" hereinafter) is used in the measurement of blood pressure information (see JP H5-39504U (Patent Literature 1)). The cuff contains a fluid bladder for pressurizing the body (an artery). The cuff is a band-shaped member having an inner cavity, and can be wrapped around a part of a body such as an upper arm.

In a blood pressure information measurement device used to measure blood pressure values such as a systolic blood pressure value or a diastolic blood pressure value (called simply a "sphygmomanometer" hereinafter), the cuff is wrapped around the surface of part of the body. A fluid such as air, a liquid, or the like is injected into or exhausted from the fluid bladder enclosed within the cuff. The fluid bladder is inflated by injecting a fluid into the fluid bladder. On the other hand, the fluid bladder is deflated by exhausting the fluid from the fluid bladder. Changes in the pressure within the fluid bladder produced when the fluid bladder inflates or deflates are registered as an arterial sphygmogram or a blood pressure value.

A typical cuff includes an air bladder serving as the fluid bladder and a band-shaped outer cover. The outer cover contains the air bladder. A surface fastener is provided on the surface of the outer cover. A loop-shaped ring is attached to one end of the outer cover in the lengthwise direction thereof. The cuff is formed into a ring shape by passing the other end of the outer cover in the lengthwise direction thereof through the loop-shaped ring and bending that other end of the outer cover back.

The measurement area is then inserted into the area of the outer cover that has been formed into a ring shape. The cuff is thus wrapped around the measurement area. The outer cover is tightened down upon the measurement area, and is held in a fastened state by the surface fastener. As a result of this fastened state, the air bladder is anchored to the measurement area. The cuff, and a sphygmomanometer provided therewith, are capable of measuring blood pressure information.

Incidentally, with a typical cuff, it is easy for the outer cover to rotate in the circumferential direction thereof when the outer cover is tightened onto the measurement area. If the outer cover rotates in the circumferential direction, it becomes necessary to rotate the outer cover in the opposite direction as the direction of the original rotation and tighten down the outer cover again in order to obtain the desired tightened state for the cuff. Typically, the stated rotation in the circumferential direction and the rotation in the opposite direction as that rotation are repeated multiple times.

Because the rotation in the circumferential direction and the rotation in the direction opposite to the circumferential direction are repeated multiple times, in the case where, for example, the blood pressure value is measured on a day-to-day basis, it is difficult to recreate a predetermined tightened state for the cuff. As a result, variations appear in the measured values obtained through day-to-day measurements, which makes it difficult to measure the blood pressure information in an accurate and stable manner.

Patent Literature 1: JP H5-39504U

SUMMARY OF INVENTION

One or more embodiments of the present invention provide a blood pressure information measurement device cuff that, when fitted to a measurement area, can repeatedly and easily recreate the same fitted state, and a blood pressure information measurement device including such a cuff.

A blood pressure information measurement device cuff according to one or more embodiments of the present invention includes a fluid bladder, an outer cover, a first guide member, and a second guide member. The fluid bladder pressurizes a body. The outer cover is band-shaped. The outer cover contains the fluid bladder on one end portion thereof. The outer cover has a first main surface and a second main surface. The second main surface opposes the body by being wrapped around the body in a circular shape. The first guide member closer to the one end portion side of the outer cover than the position in which the fluid bladder is provided. The first guide member has a portion that is formed into a circular shape for passing through and bending back another end portion of the outer cover. The second guide member is provided on the first main surface of the outer cover. The second guide member has a portion that is formed into a circular shape for passing through the other end portion of the outer cover that has been passed through the first guide member.

In a blood pressure information measurement device cuff according to one or more embodiments of the present invention, the outer cover is anchored to the body in a state in which an area of the surface of the body where the distance to an artery within the body is the shortest and the fluid bladder are disposed opposite to each other.

In a blood pressure information measurement device cuff according to one or more embodiments of the present invention, the body is an upper arm, and the second guide member is provided on the first main surface that is located toward the triceps of the upper arm when the blood pressure information measurement device cuff is anchored to the upper arm.

In a blood pressure information measurement device cuff according to one or more embodiments of the present invention, the body is one of the upper arms, and the second guide member is provided on the first main surface that is located toward the other upper arm when the blood pressure information measurement device cuff is anchored to the upper arm.

A blood pressure information measurement device cuff according to one or more embodiments of the present invention further includes a fastening member. The fastening member is provided on the first main surface. The fastening member is located between the second guide member and the first guide member, and closer to the second guide member, in the lengthwise direction of the outer cover when the outer cover is in an unrolled state.

A blood pressure information measurement device cuff according to one or more embodiments of the present invention further includes a third guide member. The third guide member is provided on the first main surface. The third guide member is located between the second guide member and the first guide member in the lengthwise direction of the outer cover when the outer cover is in an unrolled state. The other end portion that has been passed through the second guide member is passed through the third guide member.

In a blood pressure information measurement device cuff according to one or more embodiments of the present invention, the other end portion that has been passed through the third guide member is bent back in the third guide member and is then once again passed through the second guide member.

A blood pressure information measurement device cuff according to one or more embodiments of the present invention further includes a third guide member. The third guide member is provided on the first main surface. The third guide member is located between the second guide member and the other end portion in the lengthwise direction of the outer cover when the outer cover is in an unrolled state. The other end portion that has been passed through the first guide member and bent back is passed through the second guide member after being passed through the third guide member.

A blood pressure information measurement device cuff according to one or more embodiments of the present invention further includes a third guide member. The third guide member is provided on the second main surface. The third guide member is located between the second guide member and the other end portion in the lengthwise direction of the outer cover when the outer cover is in an unrolled state. The other end portion that has been passed through the second guide member is passed through the third guide member after being back in the second guide member.

A blood pressure information measurement device according to one or more embodiments of the present invention includes one of the stated blood pressure information measurement device cuffs, an inflation/deflation mechanism that inflates/deflates the fluid bladder, and a blood pressure information obtainment unit that obtains blood pressure information.

According to one or more embodiments of the present invention, it is possible to achieve a blood pressure information measurement device cuff capable of repeatedly recreating the same fitted state with ease when the cuff is fitted to a measurement area, and a blood pressure information measurement device provided with such a cuff.

DETAILED DESCRIPTION OF INVENTION

Figure 1:
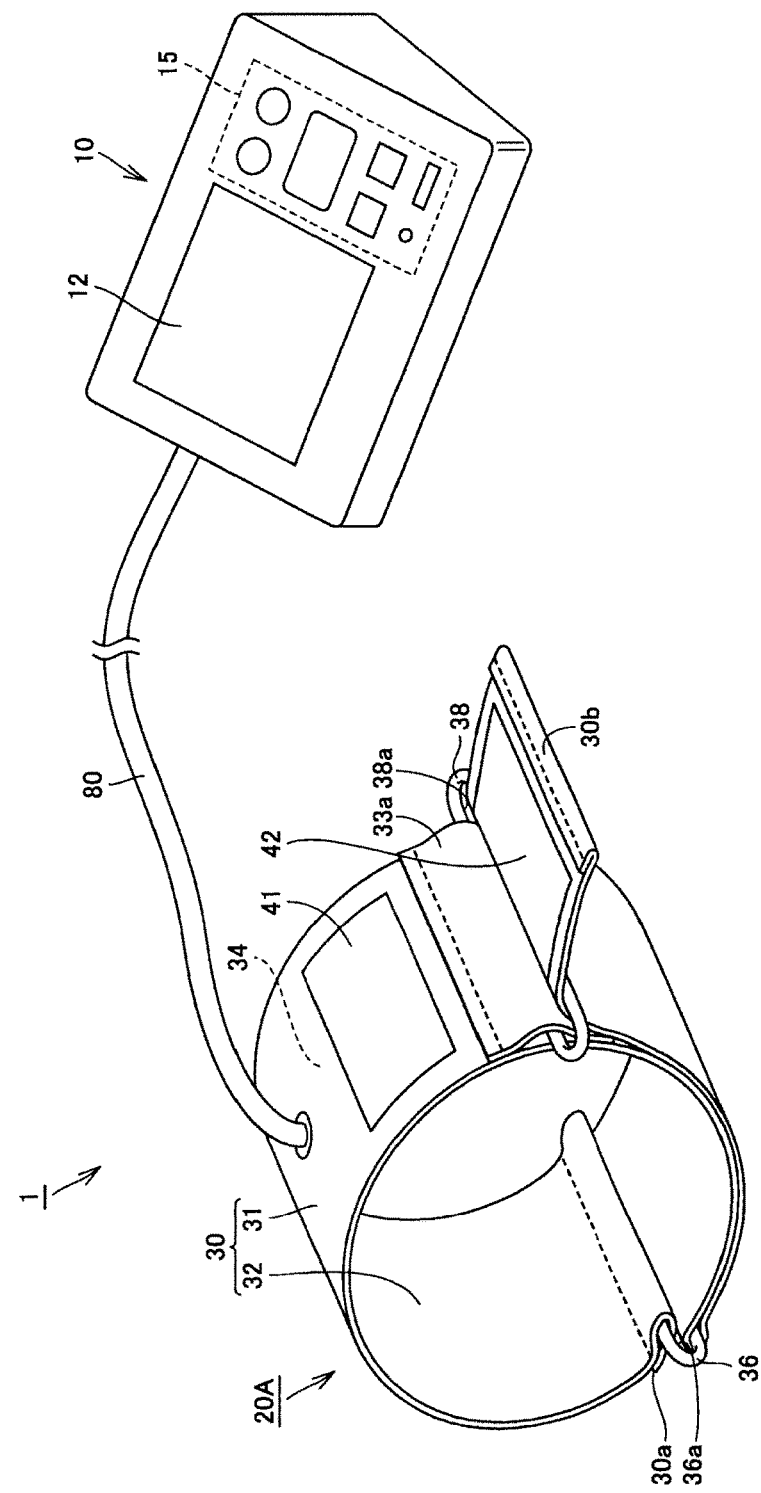
FIG. 1 is a diagram illustrating the overall configuration of a sphygmomanometer according to a first embodiment.

A blood pressure information measurement device cuff and a blood pressure information measurement device provided therewith according to one or more embodiments of the present invention will be described hereinafter with reference to the drawings.

In the following embodiments, a sphygmomanometer cuff that is used by being wrapped around an upper arm will be described as an example of the blood pressure information measurement device cuff. A sphygmomanometer capable of measuring blood pressure values such as a systolic blood pressure value and a diastolic blood pressure value using the sphygmomanometer cuff will be described as an example of the blood pressure information measurement device provided with the blood pressure information measurement device cuff.

When numbers, amounts, and so on are discussed in the following embodiment, it should be noted that unless explicitly mentioned otherwise, the scope of the present invention is not necessarily limited to those numbers, amounts, and so on. In the embodiment described hereinafter, identical and corresponding components may be assigned identical reference numerals, and redundant descriptions thereof may be omitted.

First Embodiment

A sphygmomanometer 1 according to the present embodiment will be described with reference to FIGS. 1 through 7.

Configuration of Sphygmomanometer 1

As shown in FIG. 1, the sphygmomanometer 1 includes a main body 10, a cuff 20A, and an air tube 80. The main body 10 is a box-shaped housing. A display unit 12 and an operating unit 15 are provided in the top surface of the main body 10. During measurement, the main body 10 is used by being placed on a table or the like.

The cuff 20A includes: an outer cover 30; an air bladder 34 (see FIG. 2) that is contained within the outer cover 30 as a fluid bladder; a surface fastener 41 (fastening member); a surface fastener 42; a first loop-shaped ring 36 (first guide member); and a second loop-shaped ring 38 (second guide member).

The outer cover 30 has a front surface 31 (first main surface), a rear surface 32 (second main surface), one end portion 30a, and another end portion 30b.

The outer cover 30 is configured as a bladder-shaped member in which a member that configures the front surface 31 and a member that configures the rear surface 32 are overlapped and the outer edges thereof are connected (for example, stitched, welded, or the like) together. The cuff 20A is disposed so that the rear surface 32 of the outer cover 30 and a body such as an upper arm are opposed to each other.

According to one or more embodiments of the present invention, a member that is sufficiently capable of stretching is used as the member that configures the rear surface 32 side of the outer cover 30 so that the pressurizing force applied to the upper arm by the inflation of the air bladder 34 is not inhibited.

A member that is less capable of stretching than the member of which the rear surface 32 side of the outer cover 30 is configured is used as the member that configures the front surface 31 side of the outer cover 30. Thus, a material configured of synthetic fibers such as polyamide (PA), polyester, or the like, the stretchability of which can be adjusted relatively easily, is used as the member that configures the front surface 31 side of the outer cover 30.

Figure 2:
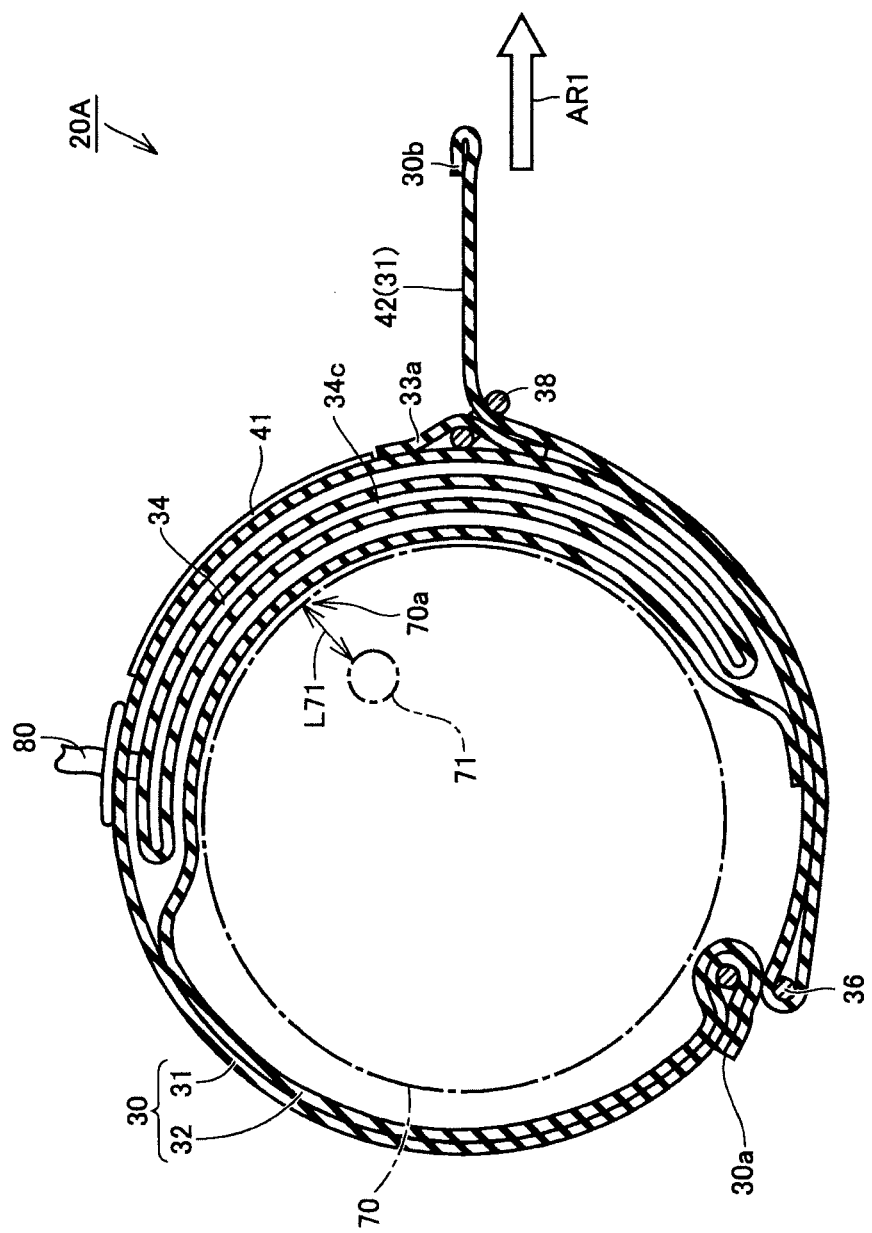
FIG. 2 is a cross-sectional view illustrating a cuff according to the first embodiment.

As shown in FIG. 2, the air bladder 34 is connected to the air tube 80. The air bladder 34 is connected to the air tube 80 while being contained within the outer cover 30. The air bladder 34 is configured of a bag-shaped member, and has, in its interior, a space that can inflate and deflate. According to one or more embodiments of the present invention, the air bladder 34 is configured using resin sheets. The air bladder 34 can be formed in a bag shape by, for example, overlaying two resin sheets and welding the edges thereof to each other.

Any material can be used for the resin sheets that configure the air bladder 34 as long as the material is stretchable and there are no leaks from the inflating/deflating space after the welding has been carried out. According to one or more embodiments of the present disclosure, the material for the resin sheets that configure the air bladder 34 is, for example, ethylene-vinyl acetate copolymer (EVA), soft polyvinyl chloride (PVC), polyurethane (PU), natural rubber (NR), or the like.

An artery 71 runs through the interior of an upper arm 70. On the surface of the upper arm 70, an area 70a is defined, in which a distance L71 between the surface of the upper arm 70 and the artery 71 is the shortest. According to one or more embodiments of the present disclosure, the outer cover 30 is anchored to the upper arm 70 in a state in which the stated area 70a and the air bladder 34 are disposed so as to oppose each other. Further, according to one or more embodiments of the present invention, the outer cover 30 is anchored to the upper arm 70 in a state in which the stated area 70a and a position 34c that is in approximately the center of the air bladder 34 are disposed so as to oppose each other.

Returning to FIG. 1, the air tube 80 connects the main body 10, which is configured separately, to the air bladder 34 that is contained within the cuff 20A. The air bladder 34 inflates as a result of a fluid being injected thereinto from the main body 10 through the air tube 80. The air bladder 34 deflates as a result of the fluid being exhausted through the air tube 80. By inflating and deflating, the air bladder 34 can apply pressure to a body such as the upper arm (not shown). According to one or more embodiments of the present invention, when the outer cover 30 (the cuff 20A) is anchored to the upper arm 70, the air tube 80 is provided in a position located toward the bicep area of the upper arm (the upper area in the drawing).

The surface fastener 41 is provided upon the front surface 31 of the outer cover 30 in an approximately rectangular shape. The surface fastener 41 is provided in a predetermined location that is between the one end portion 30a and the other end portion 30b of the outer cover 30 in the lengthwise direction thereof.

Returning to FIG. 2, according to one or more embodiments of the present invention, the surface fastener 41 is disposed between the second loop-shaped ring 38 (details will be given later) and the first loop-shaped ring 36, toward the second loop-shaped ring 38, in the lengthwise direction of the outer cover 30 when the outer cover 30 is in an unrolled state. According to one or more embodiments of the present invention, the surface fastener 41 is provided in a position between the second loop-shaped ring 38 and the first loop-shaped ring 36 that is adjacent, in the lengthwise direction of the outer cover 30 when the outer cover 30 is in an unrolled state, to an attachment cover 33a for attaching the second loop-shaped ring 38.

The surface fastener 42 is, like the surface fastener 41, provided upon the front surface 31 of the outer cover 30. The surface fastener 42 is provided toward the other end portion 30b of the outer cover 30. The surface fastener 41 and the surface fastener 42 are capable of interlocking with each other.

As shown in FIG. 1, the surface fastener 42 is provided in a partial manner on the front surface 31 of the outer cover 30. To rephrase, the surface fastener 42 and the member that configures the front surface 31 side of the outer cover 30 are configured of separate members. Instead of providing the surface fastener 42 as a separate member upon the front surface 31, the entirety of a member that configures the front surface 31 side of the outer cover 30 may serve as a member that can interlock with the surface fastener 41. According to one or more embodiments of the present invention, only the member that configures particularly the other end portion 30b side of the front surface 31 side of the outer cover 30 serves as a member that can interlock with the surface fastener 41.

The first loop-shaped ring 36 is attached near the one end portion 30a of the outer cover 30. The first loop-shaped ring 36 has an insertion hole 36a into which a portion of the outer cover 30 on the other end portion 30b side thereof can be inserted. According to one or more embodiments of the present invention, the first loop-shaped ring 36 is configured of a member that does not easily produce friction with the outer cover 30, such as a metallic member.

The first loop-shaped ring 36 is attached to the outer cover 30 by first passing a portion of the outer cover 30 on the one end portion 30a thereof through the insertion hole 36a of the first loop-shaped ring 36 and then bending back and stitching the portion of the outer cover 30 on the one end portion 30a side thereof.

The outer cover 30 is formed into a ring shape by passing the other end portion 30b of the outer cover 30 through the insertion hole 36a of the first loop-shaped ring 36. The portion of the outer cover 30 on the other end portion 30b side thereof is passed through the insertion hole 36a and is then bent back, central to the first loop-shaped ring 36, along the circumferential direction of the insertion hole 36a in the outer cover 30.

The second loop-shaped ring 38 is attached to the front surface 31 of the outer cover 30. The second loop-shaped ring 38 has an insertion hole 38a into which both a portion of the outer cover 30 on the other end portion 30b side thereof and the attachment cover 33a can be inserted. Like the first loop-shaped ring 36, according to one or more embodiments of the present invention, the second loop-shaped ring 38 is configured of a member that does not easily produce friction with the outer cover 30, such as a metallic member.

The attachment cover 33a is stitched to the front surface 31 of the outer cover 30 having been passed through the insertion hole 38a of the second loop-shaped ring 38. The second loop-shaped ring 38 is attached to the front surface 31 of the outer cover 30 by being sandwiched between the attachment cover 33a and the outer cover 30.

Referring to FIG. 2, according to one or more embodiments of the present invention, the second loop-shaped ring 38 is provided on the area of the front surface 31 that is positioned on the right side of the upper arm (the right side in FIG. 2) when the cuff 20A is anchored to the left upper arm 70. According to one or more embodiments of the present invention, the second loop-shaped ring 38 is provided on the area of the front surface 31 that is positioned furthest on the right side of the upper arm when the cuff 20A is anchored to the left upper arm 70.

The second loop-shaped ring 38 may be provided in a position where the second loop-shaped ring 38 and the air bladder 34 overlap (that is, shifted in the lengthwise direction) when viewed from above, or may be provided in a position where there is no overlap.

The other end portion 30b of the outer cover 30 that has been inserted into the first loop-shaped ring 36 and bent back is overlaid along the outer side (the front surface 31 side) of the portion of the outer cover 30 that is formed in the circular shape. The other end portion 30b is inserted into the insertion hole 38a of the second loop-shaped ring 38, and is led out toward the outer side from the portion of the outer cover 30 that is formed in the circular shape.

Figure 3:
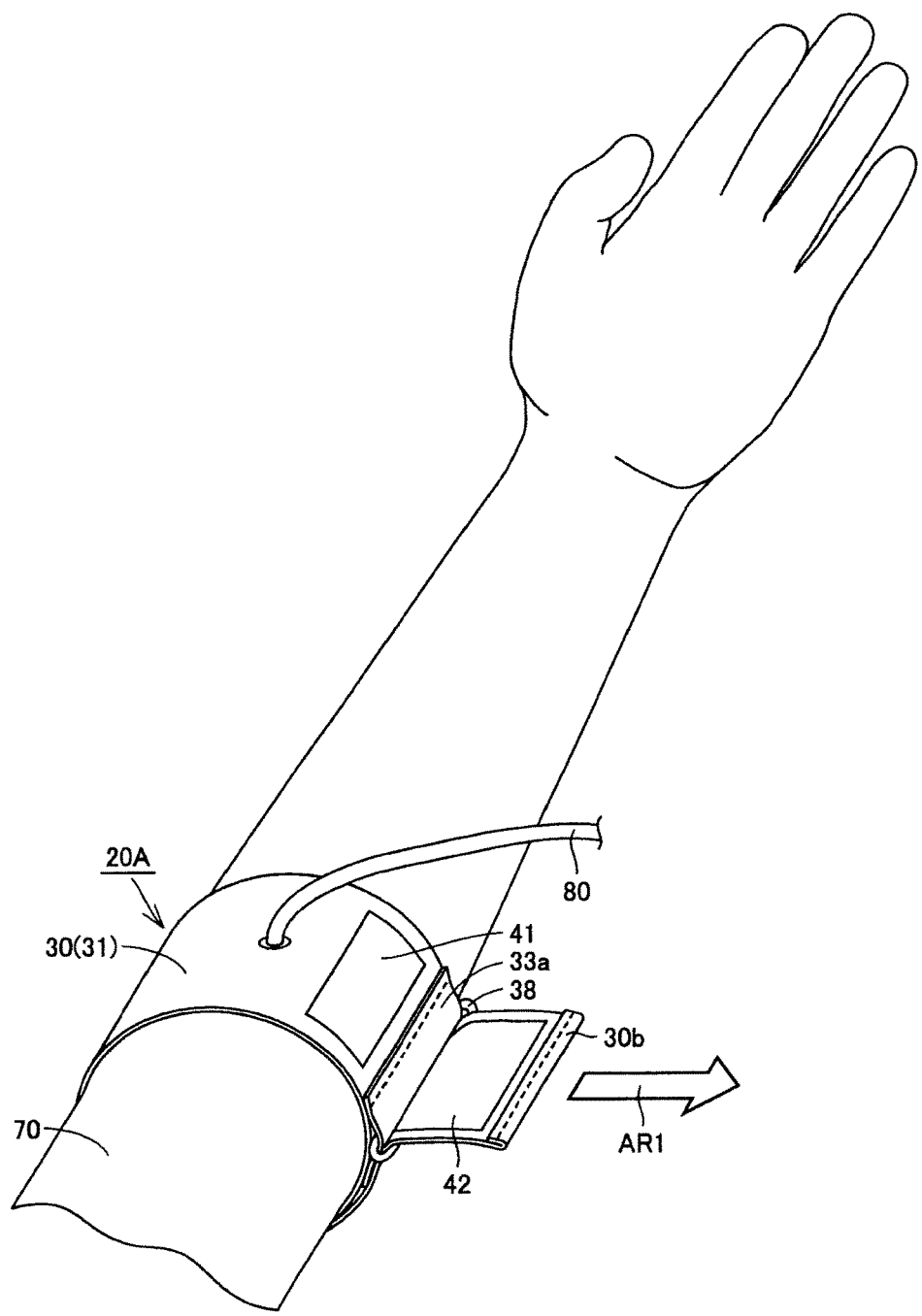
FIG. 3 is a diagram illustrating the cuff according to the first embodiment being fitted to an upper arm (a left arm).

Referring to FIG. 3, when measuring a blood pressure value using the sphygmomanometer 1 configured as described thus far, the left upper arm 70, for example, of the measurement subject is inserted into the portion of the outer cover 30 that is formed into a circular shape. The other end portion 30b of the outer cover 30 is pulled in the direction indicated by an arrow AR1 by the right hand (not shown) of the measurement subject. The outer cover 30 is then secured to the upper arm 70.

The surface fastener 41 and the surface fastener 42 are fastened to each other by overlapping, thus holding the outer cover 30 on the upper arm 70 in a secured state. The air bladder contained within the outer cover 30 is thus anchored to the upper arm 70, and the blood pressure information can then be measured.

Functional Blocks of Sphygmomanometer 1

Figure 4:
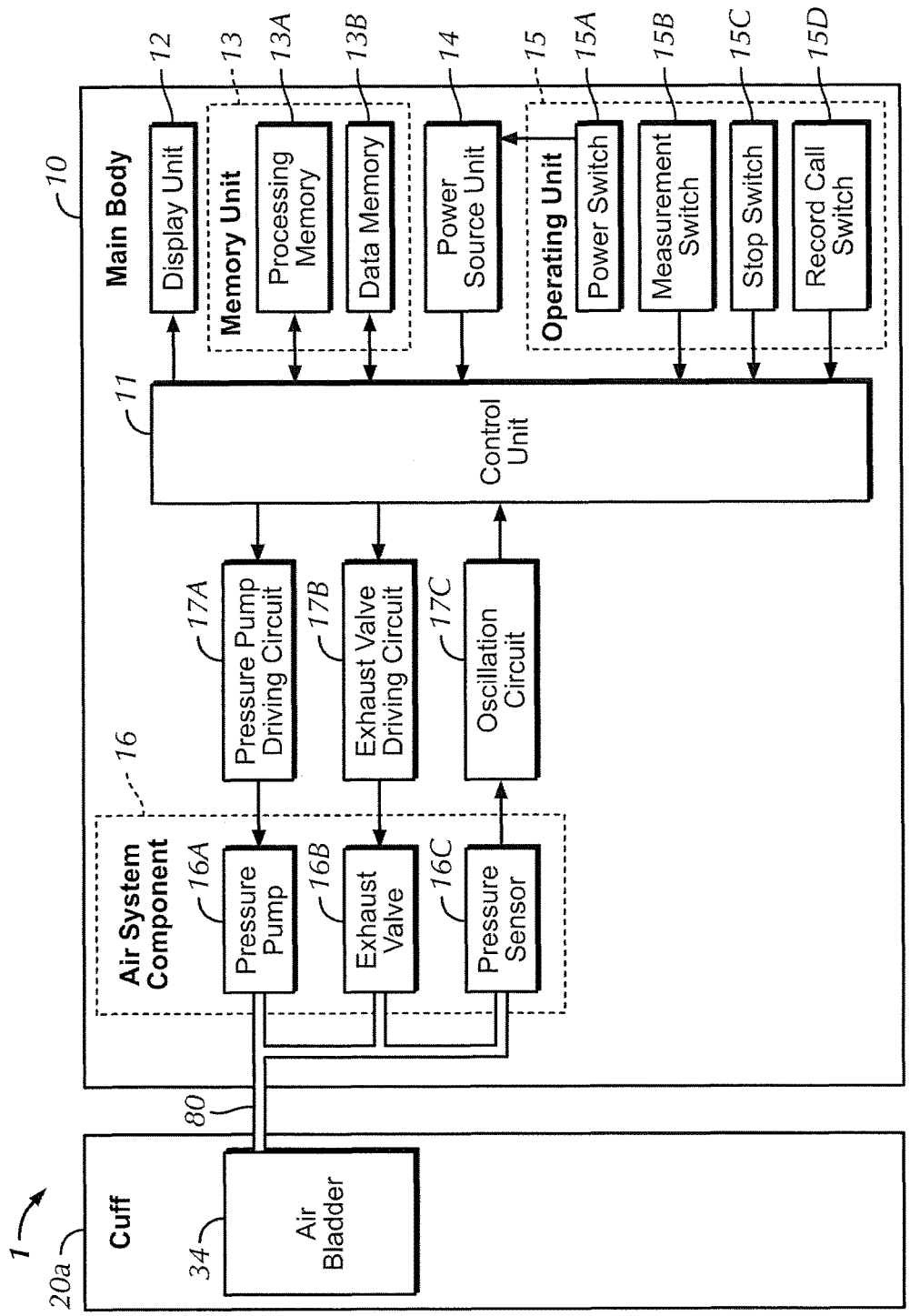
FIG. 4 is a function block diagram illustrating the sphygmomanometer according to the first embodiment.

The functional blocks of the sphygmomanometer 1 will be described with reference to FIG. 4. The main body 10 of the sphygmomanometer 1 includes, in addition to the aforementioned display unit 12 and operating unit 15, a control unit 11, a memory unit 13, a power source unit 14, a pressure pump 16a, an exhaust valve 16b, a pressure sensor 16c, a pressure pump driving circuit 17a, an exhaust valve driving circuit 17b, and an oscillation circuit 17c.

The pressure pump 16a, exhaust valve 16b, and pressure sensor 16c correspond to an air system component 16 of the sphygmomanometer 1. The pressure pump 16a and exhaust valve 16b correspond to an inflation/deflation mechanism in the sphygmomanometer 1 for inflating and deflating the air bladder 34.

The air bladder 34 has an inflation/deflation space, serving as a cavity, in its interior, as described above. The air bladder 34 is connected to the pressure pump 16a, the exhaust valve 16b, and the pressure sensor 16c, respectively, via the air tube 80.

The control unit 11 is configured of, for example, a CPU (central processing unit). The control unit 11 controls the sphygmomanometer 1 as a whole. The display unit 12 is configured of, for example, an LCD (liquid-crystal display). The display unit 12 displays measurement results and the like.

The memory unit 13 is configured of a processing memory 13a and a data memory 13b. Using the processing memory 13a and the data memory 13b, the memory unit 13 stores programs for causing the control unit 11 to carry out processes for blood pressure value measurement, stores measurement results and the like, and so on.

The power source unit 14 supplies electricity, as a power source, to the control unit 11. The operating unit 15 is configured of a power switch 15a, a measurement switch 15b, a stop switch 15c, and a record call switch 15d. The operating unit 15 accepts operations of the switches 15a through 15d from a measurement subject or the like, and inputs commands from the exterior into the control unit 11 or the power source unit 14.

The control unit 11 inputs control signals for driving the pressure pump 16a and the exhaust valve 16b into the pressure pump driving circuit 17a and the exhaust valve driving circuit 17b, respectively. The control unit 11 inputs a blood pressure value, serving as a measurement result, into the memory unit 13 or the display unit 12.

The control unit 11 includes a blood pressure information obtainment unit (not shown) that obtains a blood pressure value of the measurement subject based on a pressure value detected by the pressure sensor 16c. The blood pressure value obtained by the blood pressure information obtainment unit is inputted into the aforementioned memory unit 13 or the display unit 12 as a measurement result.

The sphygmomanometer 1 may also include a separate output unit that outputs a blood pressure value to an external device (for example, a PC (personal computer), a printer, or the like) as the measurement result. For example, a serial communication line, a device that writes to various types of recording media, or the like can be used as the output unit.

The inflation/deflation operations performed by the pressure pump 16a are controlled by the pressure pump driving circuit 17a based on the control signal inputted from the control unit 11. The pressure pump 16a increases the pressure within the air bladder 34 (this will be called a "cuff pressure" hereinafter) by supplying a fluid such as air to the inner cavity of the air bladder 34.

The opening/closing operations of the exhaust valve 16b are controlled by the exhaust valve driving circuit 17b based on the control signal inputted from the control unit 11. The exhaust valve 16b maintains the cuff pressure, decreases the cuff pressure by opening the inner cavity of the air bladder 34 to the exterior, and so on.

The pressure sensor 16c inputs, to the oscillation circuit 17c, an output signal based on the pressure within the air bladder 34. The oscillation circuit 17c generates an oscillation frequency signal in accordance with the signal inputted from the pressure sensor 16c, and inputs the generated signal to the control unit 11.

Flow of Processing of Sphygmomanometer 1

Figure 5:
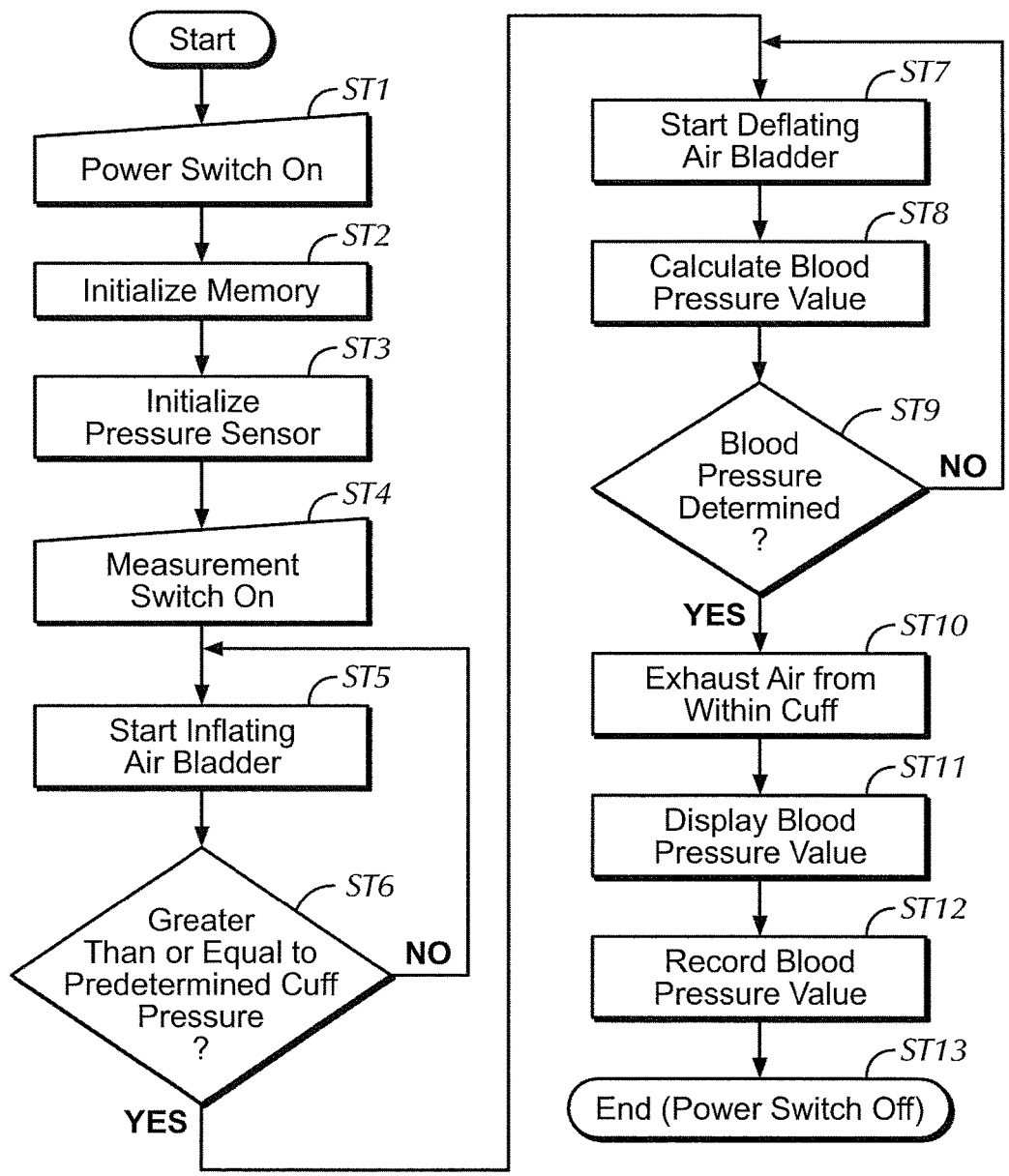
FIG. 5 is a diagram illustrating the flow of processing performed by the sphygmomanometer according to the first embodiment.

A flow of processing performed by the sphygmomanometer 1 will be described with reference to FIG. 4 and FIG. 5. A program that follows the flow of the processing performed by the sphygmomanometer 1 is stored in advance in the memory unit 13. The processing of the sphygmomanometer 1 is executed by the control unit 11 reading out this program from the memory unit 13 and executing the program.

When measuring a blood pressure value, the measurement subject first attaches the cuff 20A to his or her upper arm. In this state, the measurement subject manipulates the operating unit 15 (the power switch 15a) provided in the main body 10, and turns the sphygmomanometer 1 on (step ST1).

Electricity, serving as a power source, is supplied from the power source unit 14 to the control unit 11, thus driving the control unit 11. The control unit 11 then initializes the memory unit 13 (step ST2). Next, the control unit 11 initializes the pressure sensor 16c (step ST3).

The control unit 11 then stands by for an instruction to start the measurement from the measurement subject. As an instruction to start the measurement, the measurement subject manipulates the operating unit 15 (the measurement switch 15b) (step ST4). The control unit 11 closes the exhaust valve 16b and drives the pressure pump 16a. The inflation of the air bladder 34 is started (step ST5).

The cuff pressure in the air bladder 34 rises. The cuff pressure in the air bladder 34 then becomes greater than or equal to a predetermined cuff pressure required for blood pressure value measurement (step ST6). The control unit 11 then stops the pressure pump 16a and opens the exhaust valve 16b that was closed. The air within the air bladder 34 is exhausted, and the air bladder 34 gradually begins to deflate (step ST7).

With the sphygmomanometer 1, the blood pressure value is measured while the cuff pressure is gradually decreasing. The sphygmomanometer 1 calculates a blood pressure value, such as a systolic blood pressure value, a diastolic blood pressure value, or the like, using the control unit 11 (step ST8).

The control unit 11 extracts sphygmogram information based on an oscillation frequency obtained from the oscillation circuit 17c while the cuff pressure of the air bladder 34 is gradually decreasing. The control unit 11 determines the blood pressure value based on the extracted sphygmogram information (step ST9).

When the blood pressure value is determined, the control unit 11 opens the air bladder 34 and completely exhausts the air from within the air bladder 34 (step ST10). The control unit 11 then displays the blood pressure value, serving as a measurement result, in the display unit 12 (step ST11). The control unit 11 then stores the blood pressure value in the memory unit 13, and records that value as data (step ST12).

The measurement subject and then operates the operating unit 15 (the power switch 15a) provided in the main body 10, and turns the sphygmomanometer 1 off. Turning the sphygmomanometer 1 off ends the operations thereof (step ST13).

The measurement method described thus far is what is known as a deflation measurement method, which detects a sphygmogram while the air bladder 34 is deflating. However, the measurement method for the sphygmomanometer 1 is not limited to the deflation measurement method, and what is known as an inflation measurement method, which detects a sphygmogram while the air bladder 34 is inflating, can also be employed.

Actions and Effects

Figure 6:
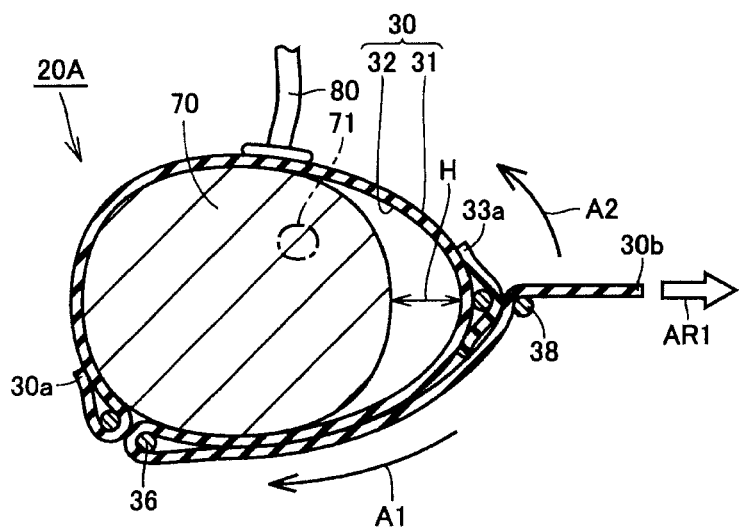
FIG. 6 is a first cross-sectional view illustrating, over time, the fitting of the cuff according to the first embodiment onto an upper arm.
Figure 7:
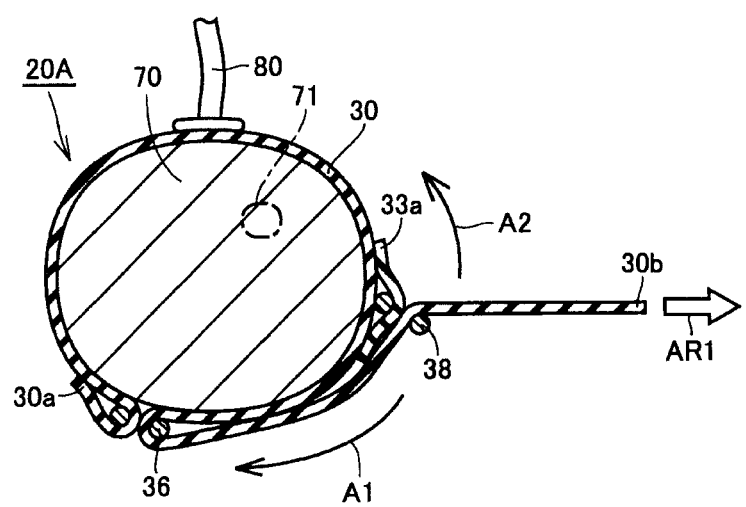
FIG. 7 is a second cross-sectional view illustrating, over time, the fitting of the cuff according to the first embodiment onto an upper arm.

Actions and effects of the present embodiment will be described with reference to FIGS. 6 and 7. FIGS. 6 and 7 are cross-sectional views illustrating, over time, the fitting (process of fitting) of the sphygmomanometer cuff 20A according to the present embodiment to the upper arm 70. The state shown in FIG. 6 progresses to the state shown in FIG. 7. In FIGS. 6 and 7, the air bladder 34 is not shown. In actuality, the air bladder 34 is disposed in the manner shown in FIG. 2.

As shown in FIG. 6, with the cuff 20A, the left upper arm 70, for example, of the measurement subject is inserted into the portion of the outer cover 30 that is formed into a circular shape. After the upper arm 70 has been inserted, the other end portion 30b of the outer cover 30 is gripped by the right hand. The gripped other end portion 30b is then pulled in the direction indicated by the arrow AR1. Because the second loop-shaped ring 38 is provided on the front surface 31 in a position located toward the right upper arm side (the right side in the drawings), the measurement subject can easily pull the other end portion 30b using his or her right hand.

When the other end portion 30b is pulled in the direction indicated by the arrow AR1, the second loop-shaped ring 38 is also pulled in the direction indicated by the arrow AR1 by the other end portion 30b side of the outer cover 30. A gap H is formed between the upper arm 70 and the portion of the outer cover 30 that is formed into a circular shape toward the side where the second loop-shaped ring 38 is provided.

In order to achieve a desired tightened state for the cuff 20A, the other end portion 30b of the outer cover 30 is pulled by the right hand in the direction indicated by the arrow AR1. The diameter of the portion of the outer cover 30 formed into a circular shape gradually decreases. The gap H also gradually decreases.

When the diameter of the portion of the outer cover 30 that is formed into a circular shape gradually decreases, the portion on the side of the outer cover 30 that is to be inserted into the first loop-shaped ring 36 (the side toward the bottom in the drawings) slides against the surface of the upper arm 70 (toward the left in the drawings) while making contact with the upper arm 70.

As a result, the portion of the outer cover 30 on the side where the second loop-shaped ring 38 is provided (what is essentially the right half of the outer cover 30 in the drawings) is pulled toward the first loop-shaped ring 36, and attempts to rotate in the direction indicated by the arrow A1 (the clockwise direction). A force that attempts to rotate the second loop-shaped ring 38 in the direction indicated by the arrow A1 (the clockwise direction) acts on the second loop-shaped ring 38.

Here, as described above, a force that attempts to move the second loop-shaped ring 38 in the direction indicated by the arrow AR1 also acts on the second loop-shaped ring 38. This force acts so as to continually position the second loop-shaped ring 38 on the rightmost side of the upper arm 70. This force works reactively in the direction indicated by an arrow A2 (the counter-clockwise direction), against the force that attempts to rotate the second loop-shaped ring 38 in the direction indicated by the arrow A1 (the clockwise direction).

In other words, two forces act on the second loop-shaped ring 38: the force that attempts to rotate the second loop-shaped ring 38 in the clockwise direction, and the force that works in the counter-clockwise direction reactively against that force. These forces cancel each other out, and thus the position of the second loop-shaped ring 38 in the circumferential direction relative to the upper arm 70 experiences almost no change. Accordingly, the diameter of the portion of the outer cover 30 that is formed in a circular shape can be reduced with the position of the second loop-shaped ring 38 in the circumferential direction relative to the upper arm 70 experiencing almost no change.

As shown in FIG. 7, the outer cover 30 and the upper arm 70 come into tight contact with each other, and thus the gap H is essentially eliminated. This completes the securing of the cuff 20A to the upper arm 70.

Here, the second loop-shaped ring 38 is provided on the front surface 31 of the outer cover 30. The first loop-shaped ring 36 is passed through the insertion hole 38a of the second loop-shaped ring 38, and the other end portion 30b of the outer cover 30 that has been bent back is passed through the first loop-shaped ring 36. The portion of the outer cover 30 in which the attachment cover 33a is provided is continuous with the portion of the outer cover 30 that contains the air bladder 34. As a result, the second loop-shaped ring 38 and the air bladder 34 move relationally (that is, in tandem) in the circumferential direction.

As described above, the position of the second loop-shaped ring 38 relative to the upper arm 70 experiences almost no change between before and after the outer cover 30 is secured to the upper arm 70. Therefore, the position of the air bladder 34 relative to the upper arm 70 also experiences almost no change between before and after the outer cover 30 is secured to the upper arm 70.

As described initially, the rotation in the circumferential direction and the rotation in the opposite direction as that rotation are not repeated from when the sphygmomanometer cuff 20A is secured to after the sphygmomanometer cuff 20A is secured. Even if the cuff 20A is secured to the upper arm 70 on a daily basis, the second loop-shaped ring 38 is, by design, repeatedly disposed in approximately the same position near the rightmost side of the upper arm 70. Thus the air bladder 34 can also, by design, be repeatedly disposed in approximately the same position. This makes it possible to repeatedly recreate a predetermined tightened state for the cuff 20A.

According to the cuff 20A and the sphygmomanometer 1 provided therewith, the occurrence of measurement errors caused by shifts in the fitting position is reduced, which makes it possible to measure the blood pressure information in an accurate and stable manner without variations occurring in the measured values.

As shown in FIG. 2 and as described above, according to one or more embodiments of the present invention, the surface fastener 41 is positioned between the second loop-shaped ring 38 and the first loop-shaped ring 36 and toward the second loop-shaped ring 38. Through this configuration, the surface fastener 41 is positioned more toward the one end portion 30a of the outer cover 30 than the second loop-shaped ring 38. The surface fastener 41 and the surface fastener 42 are thus capable of interlocking with ease.

First Variation on First Embodiment

Figure 8:
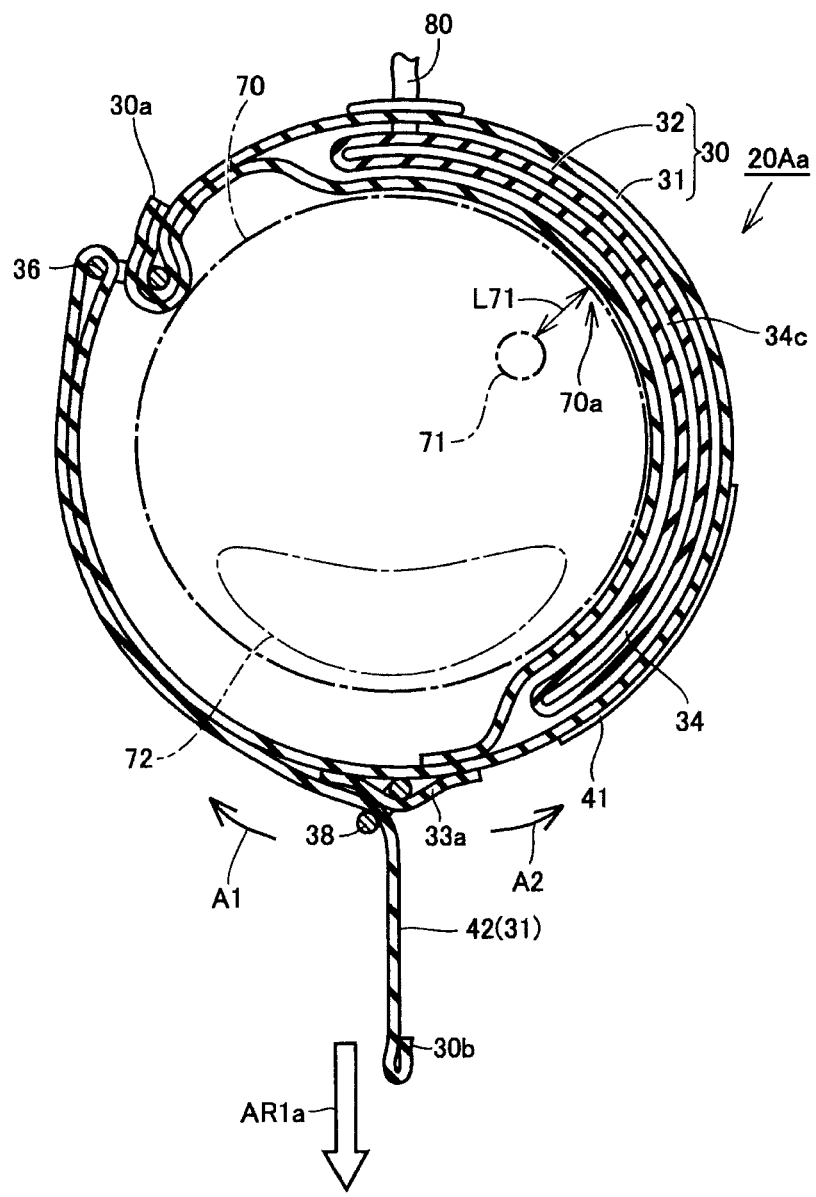
FIG. 8 is a cross-sectional view illustrating a cuff according to a first variation on the first embodiment.

A cuff 20Aa according to a first variation on the first embodiment will be described with reference to FIG. 8. The second loop-shaped ring 38 may be provided on an area of the front surface 31 that is positioned on the side of the triceps 72 of the upper arm (that is, the lower side in the drawings) when the cuff 20Aa is anchored to the upper arm.

With the cuff 20Aa, the left upper arm 70, for example, of the measurement subject is inserted into the portion of the outer cover 30 that is formed into a circular shape. After the upper arm 70 has been inserted, the other end portion 30b of the outer cover 30 is gripped by the right hand. The gripped other end portion 30b is then pulled in the direction indicated by an arrow AR1a.

When the other end portion 30b is pulled in the direction indicated by the arrow AR1a, the second loop-shaped ring 38 is also pulled in the direction indicated by the arrow AR1a by the other end portion 30b side of the outer cover 30.

When the diameter of the portion of the outer cover 30 that is formed into a circular shape gradually decreases, the portion on the side of the outer cover 30 that is to be inserted into the first loop-shaped ring 36 (the side toward the left in the drawings) slides against the surface of the upper arm 70 (upward in the drawings) while making contact with the upper arm 70.

As a result, the portion of the outer cover 30 on the side where the second loop-shaped ring 38 is provided (what is essentially the lower half of the outer cover 30 in the drawings) is pulled toward the first loop-shaped ring 36, and attempts to rotate in the direction indicated by the arrow A1 (the clockwise direction). A force that attempts to rotate the second loop-shaped ring 38 in the direction indicated by the arrow A1 (the clockwise direction) acts on the second loop-shaped ring 38.

Here, as described above, a force that attempts to move the second loop-shaped ring 38 in the direction indicated by the arrow AR1a also acts on the second loop-shaped ring 38. This force acts so as to continually position the second loop-shaped ring 38 furthest toward the triceps 72 side of the upper arm 70. This force works reactively in the direction indicated by the arrow A2 (the counter-clockwise direction), against the force that attempts to rotate the second loop-shaped ring 38 in the direction indicated by an arrow A1a (the clockwise direction).

In other words, two forces act on the second loop-shaped ring 38: the force that attempts to rotate the second loop-shaped ring 38 in the clockwise direction, and the force that works in the counter-clockwise direction reactively against that force. These forces cancel each other out, and thus the position of the second loop-shaped ring 38 in the circumferential direction relative to the upper arm 70 experiences almost no change. Accordingly, the diameter of the portion of the outer cover 30 that is formed in a circular shape can be reduced with the position of the second loop-shaped ring 38 in the circumferential direction relative to the upper arm 70 experiencing almost no change.

As in the aforementioned first embodiment, the portion of the outer cover 30 in which the attachment cover 33a is provided is continuous with the portion of the outer cover 30 that contains the air bladder 34. The position of the air bladder 34 relative to the upper arm 70 also experiences almost no change between before and after the outer cover 30 is secured to the upper arm 70.

As described initially, the rotation in the circumferential direction and the rotation in the opposite direction as that rotation are not repeated before and after the sphygmomanometer cuff 20Aa is secured. This makes it possible to repeatedly recreate a predetermined tightened state for the cuff 20Aa.

According to the cuff 20Aa and the sphygmomanometer 1 provided therewith, the occurrence of measurement errors caused by shifts in the fitting position is reduced, which makes it possible to measure the blood pressure information in an accurate and stable manner without variations occurring in the measured values.

Second Variation on First Embodiment

As shown in FIG. 1, in the first embodiment, the cuff 20A includes the outer cover 30, the air bladder 34 (see FIG. 2), the surface fastener 41, the surface fastener 42, the first loop-shaped ring 36 (first guide member), and the second loop-shaped ring 38 (second guide member).

Figure 9:
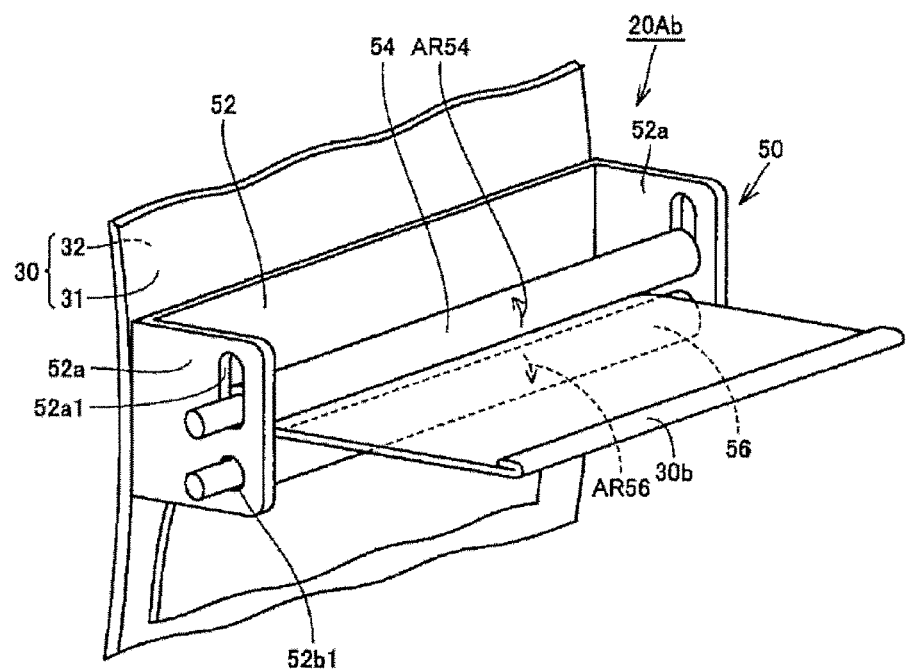
FIG. 9 is a partial perspective view illustrating a cuff according to a second variation on the first embodiment.

Meanwhile, as shown in FIG. 9, a cuff 20Ab according to a second variation on the first embodiment differs from the cuff 20A according to the first embodiment in that the surface fasteners 41 and 42 are not provided. The cuff 20Ab includes an anchoring member 50 that serves as the second guide member. The outer cover 30 is held in a secured state by the anchoring member 50.

The anchoring member 50 includes a support frame 52, a first roller 54, a second roller 56, and a predetermined engagement means (details of which will be given later). The anchoring member 50 is attached to the front surface 31 of the outer cover 30. Specifically, the support frame 52 of the anchoring member 50 is attached to the front surface 31 of the outer cover 30.

The support frame 52 is formed by carrying out a pressing process on both ends of, for example, a metallic plate-shaped member. The support frame 52 has side wall portions 52a and 52a on both sides thereof in the lengthwise direction (the direction that follows the width direction of the cuff 20Ab). An oval-shaped shaft support hole 52a1 is provided in each side wall portion 52a. Furthermore, a circular shaft support hole 52b1 is provided in each side wall portion 52a.

The first roller 54 is provided so as to extend along the width direction of the cuff 20Ab. Each end of the first roller 54 is inserted into a respective shaft support hole 52a1. The first roller 54 is supported in a rotatable state by the side wall portions 52a (the shaft support holes 52a1) in the support frame 52.

The second roller 56 is, like the first roller 54, provided so as to extend along the width direction of the cuff 20Ab. Each end of the second roller 56 is inserted into a respective shaft support hole 52b1. The second roller 56 is supported in a rotatable state by the side wall portions 52a (the shaft support holes 52b1).

The other end portion 30b side of the outer cover 30 can be passed through an insertion hole defined by the side wall portions 52a and 52a of the support frame 52, the first roller 54, and the second roller 56.

The other end portion 30b of the outer cover 30 that has been passed through the first loop-shaped ring 36 (see FIG. 1) is overlaid along the outer side (the front surface 31 side) of the portion of the outer cover 30 that is formed into a circular shape. The other end portion 30b is inserted between the first roller 54 and the second roller 56, and is led out toward the outer side from the portion of the outer cover 30 that is formed into the circular shape.

The outer cover 30 is secured to the body by the other end portion 30b of the outer cover 30 being pulled in the direction away from the anchoring member 50.

According to one or more embodiments of the present invention, the engagement means for holding the outer cover 30 in a secured state against the body is configured, for example, so as to bias the first roller 54 toward the second roller 56. The engagement means may alternatively be configured so that the first roller 54 can rotate only in the direction indicated by an arrow AR54 and the second roller 56 can rotate only in the direction indicated by an arrow AR56.

By employing the anchoring member 50 as the engagement means, the anchoring member 50 holds the outer cover 30 in a secured state against the body. According to the cuff 20Ab, it is not necessary to provide the surface fasteners.

As described initially, the rotation in the circumferential direction and the rotation in the opposite direction as that rotation are not repeated before and after the sphygmomanometer cuff 20Ab is secured. Even if the cuff 20Ab is secured to the upper arm on a daily basis, the anchoring member 50 is, by design, repeatedly disposed in approximately the same position near the rightmost side of the upper arm. Thus, the air bladder 34 can also, by design, be repeatedly disposed in approximately the same position. This makes it possible to repeatedly recreate a predetermined tightened state for the cuff 20Ab.

According to the cuff 20Ab and a sphygmomanometer provided therewith, the occurrence of measurement errors caused by shifts in the fitting position is reduced, which makes it possible to measure the blood pressure information in an accurate and stable manner without variations occurring in the measured values.

Third Variation on First Embodiment

Figure 10:
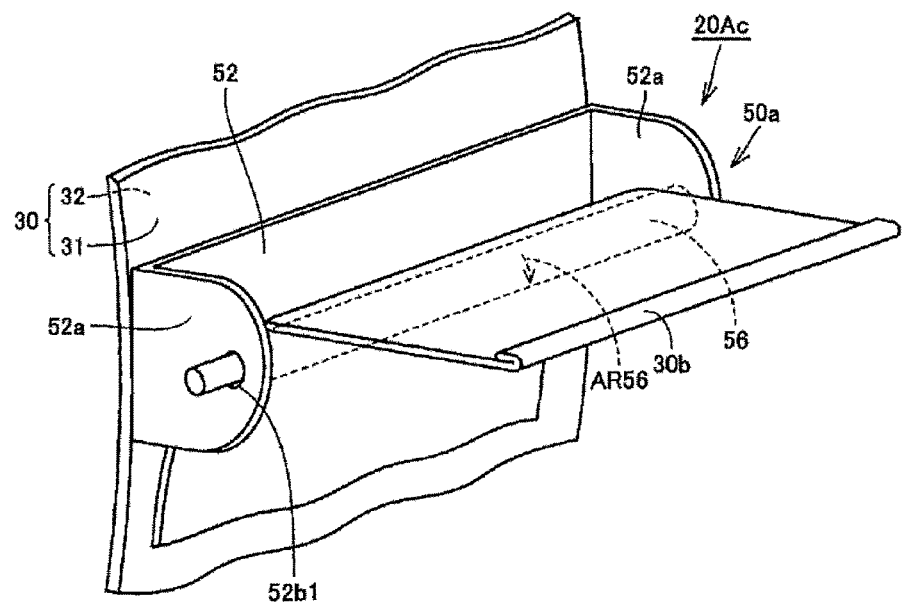
FIG. 10 is a partial perspective view illustrating a cuff according to a third variation on the first embodiment.

A cuff 20Ac according to a third variation on the first embodiment will be described with reference to FIG. 10. Here, the differences between the cuff 20Ac and the cuff 20Ab according to the second variation on the first embodiment will be described.

The cuff 20Ac includes an anchoring member 50a that serves as the second guide member. The anchoring member 50a includes the second roller 56. The anchoring member 50a does not include the first roller 54 (see FIG. 9).

The other end portion 30b of the outer cover 30 that has been passed through the first loop-shaped ring 36 (see FIG. 1) is overlaid along the outer side (the front surface 31 side) of the portion of the outer cover 30 that is formed into a circular shape.

The other end portion 30b is inserted between the second roller 56 and the support frame 52, and is led out toward the outer side from the portion of the outer cover 30 that is formed into the circular shape.

The outer cover 30 is secured to the body by the other end portion 30b of the outer cover 30 being pulled in the direction away from the anchoring member 50a.

According to one or more embodiments of the present invention, the configuration is such that the second roller 56 can rotate only in the direction indicated by the arrow AR56, in order to hold the outer cover 30 in a secured state against the body. The cuff 20Ac may, as with the aforementioned first embodiment, include a surface fastener (not shown) as the engagement means.

According to the cuff 20Ac and a sphygmomanometer provided therewith as well, the occurrence of measurement errors caused by shifts in the fitting position is reduced, which makes it possible to measure the blood pressure information in an accurate and stable manner without variations occurring in the measured values.

Second Embodiment

Figure 11:
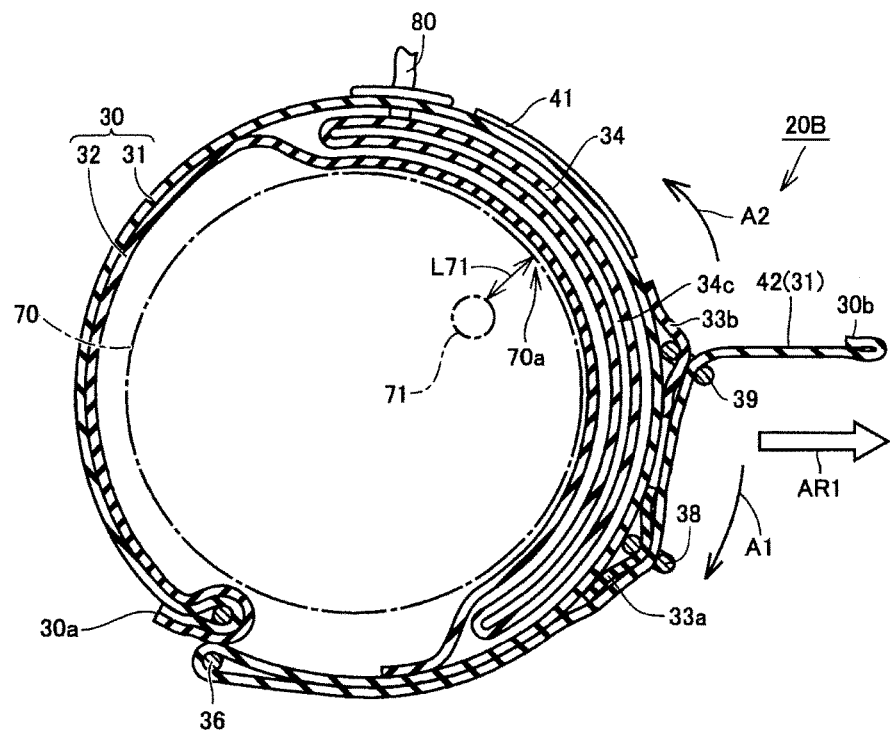
FIG. 11 is a cross-sectional view illustrating a cuff according to a second embodiment.
Figure 12:
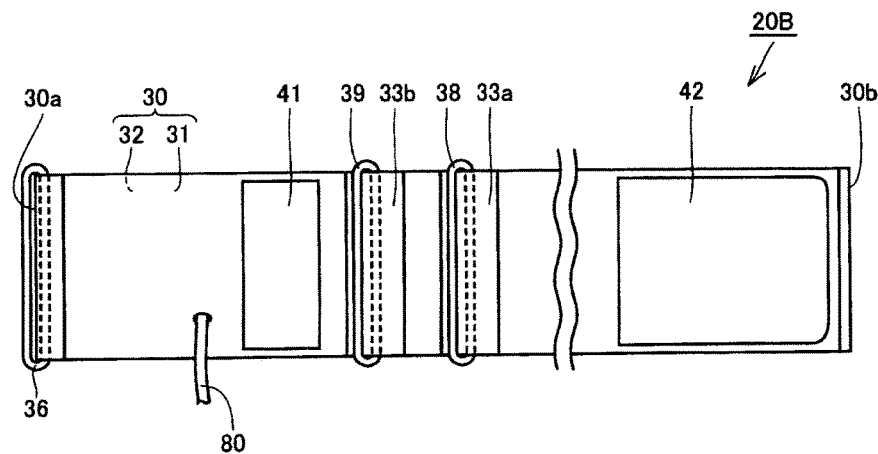
FIG. 12 is a plan view illustrating the cuff according to the second embodiment in an unrolled state.

A sphygmomanometer according to a second embodiment will be described with reference to FIGS. 11 and 12. Here, only the differences from the first embodiment will be described. The difference between the first embodiment and the present embodiment lies in that a cuff 20B further includes a third loop-shaped ring 39. In FIG. 12, the air bladder 34 is not shown. In actuality, the air bladder 34 is, as shown in FIG. 11, contained within the outer cover 30. The same applies to FIGS. 14, 16, and 18, described later.

The third loop-shaped ring 39 is attached to the front surface 31 of the outer cover 30. The third loop-shaped ring 39 is configured in essentially the same manner as the second loop-shaped ring 38. Specifically, the third loop-shaped ring 39 includes a portion on the other end portion 30b side of the outer cover 30, and an insertion hole through which an attachment cover 33b can be passed. According to one or more embodiments of the present invention, the third loop-shaped ring 39 is configured of a member that does not easily produce friction with the outer cover 30, such as a metallic member.

The attachment cover 33b is stitched to the front surface 31 of the outer cover 30 having been passed through the insertion hole of the third loop-shaped ring 39. The third loop-shaped ring 39 is attached to the front surface 31 of the outer cover 30 by being sandwiched between the attachment cover 33b and the outer cover 30.

As shown in FIG. 12, the third loop-shaped ring 39 is located between the first loop-shaped ring 36 and the second loop-shaped ring 38 in the lengthwise direction of the outer cover 30 when the outer cover 30 is in an unrolled state.

As shown in FIG. 11, the other end portion 30b of the outer cover 30 that has been passed through the first loop-shaped ring 36 is overlaid along the outer side (the front surface 31 side) of the portion of the outer cover 30 that is formed into a circular shape. The other end portion 30b is passed through the insertion hole 38a of the second loop-shaped ring 38.

The other end portion 30b of the outer cover 30 that has been passed through the insertion hole 38a of the second loop-shaped ring 38 is overlaid along the outer side (the front surface 31 side) of the portion of the outer cover 30 that is formed into a circular shape. The other end portion 30b is passed through the insertion hole of the third loop-shaped ring 39, and is led out toward the outer side from the portion of the outer cover 30 that is formed in the circular shape.

Actions and Effects

With the cuff 20B, the left upper arm 70, for example, of the measurement subject is inserted into the portion of the outer cover 30 that is formed into a circular shape. After the upper arm 70 has been inserted, the other end portion 30b of the outer cover 30 is gripped by the right hand (not shown). The gripped other end portion 30b is then pulled in the direction indicated by the arrow AR1.

When the other end portion 30b is pulled in the direction indicated by the arrow AR1, the third loop-shaped ring 39 is also pulled in the direction indicated by the arrow AR1 by the other end portion 30b side of the outer cover 30.

In order to achieve a desired tightened state for the cuff 20B, the other end portion 30b of the outer cover 30 is pulled by the right hand in the direction indicated by the arrow AR1. The diameter of the portion of the outer cover 30 formed into a circular shape gradually decreases.

The portion of the outer cover 30 on the side where the second loop-shaped ring 38 and the third loop-shaped ring 39 are provided (what is essentially the right half of the outer cover 30 in the drawings) is pulled toward the first loop-shaped ring 36, and attempts to rotate in the direction indicated by the arrow A1 (the clockwise direction). A force that attempts to rotate the third loop-shaped ring 39 in the direction indicated by the arrow A1 (the clockwise direction) acts on the third loop-shaped ring 39.

Here, as described above, a force that attempts to move the third loop-shaped ring 39 in the direction indicated by the arrow AR1 also acts on the third loop-shaped ring 39. This force acts so as to continually position the third loop-shaped ring 39 on the rightmost side of the upper arm 70. This force works reactively in the direction indicated by the arrow A2 (the counter-clockwise direction), against the force that attempts to rotate the third loop-shaped ring 39 in the direction indicated by the arrow A1 (the clockwise direction).

In other words, two forces act on the third loop-shaped ring 39: the force that attempts to rotate the third loop-shaped ring 39 in the clockwise direction, and the force that works in the counter-clockwise direction reactively against that force. These forces cancel each other out, and thus the position of the third loop-shaped ring 39 in the circumferential direction relative to the upper arm 70 experiences almost no change. Accordingly, the diameter of the portion of the outer cover 30 that is formed in a circular shape can be reduced with the position of the third loop-shaped ring 39 in the circumferential direction relative to the upper arm 70 experiencing almost no change.

The outer cover 30 and the upper arm 70 come into tight contact with each other, thus completing the securing of the cuff 20B to the upper arm 70.

Here, the third loop-shaped ring 39 is located between the first loop-shaped ring 36 and the second loop-shaped ring 38 in the lengthwise direction. The portion of the outer cover 30 in which the attachment cover 33b is provided is continuous with the portion of the outer cover 30 that contains the air bladder 34. As a result, the third loop-shaped ring 39 and the air bladder 34 move relationally (that is, in tandem) in the circumferential direction.

As described above, the position of the third loop-shaped ring 39 relative to the upper arm 70 experiences almost no change between before and after the outer cover 30 is secured to the upper arm 70. Therefore, the position of the air bladder 34 relative to the upper arm 70 also experiences almost no change between before and after the outer cover 30 is secured to the upper arm 70.

As described initially, the rotation in the circumferential direction and the rotation in the opposite direction as that rotation are not repeated before and after the sphygmomanometer cuff 20B is secured. Even if the cuff 20B is secured to the upper arm 70 on a daily basis, the third loop-shaped ring 39 is, by design, repeatedly disposed in approximately the same position near the rightmost side of the upper arm 70. The air bladder 34 can also, by design, be repeatedly disposed in approximately the same position, which makes it possible to repeatedly recreate a predetermined tightened state for the cuff 20B.

According to the cuff 20B and a sphygmomanometer provided therewith, the occurrence of measurement errors caused by shifts in the fitting position is reduced, which makes it possible to measure the blood pressure information in an accurate and stable manner without variations occurring in the measured values.

Variation on Second Embodiment

A sphygmomanometer according to a variation on the second embodiment will be described with reference to FIGS. 13 and 14. Here, only the differences from the second embodiment will be described.

Figure 13:
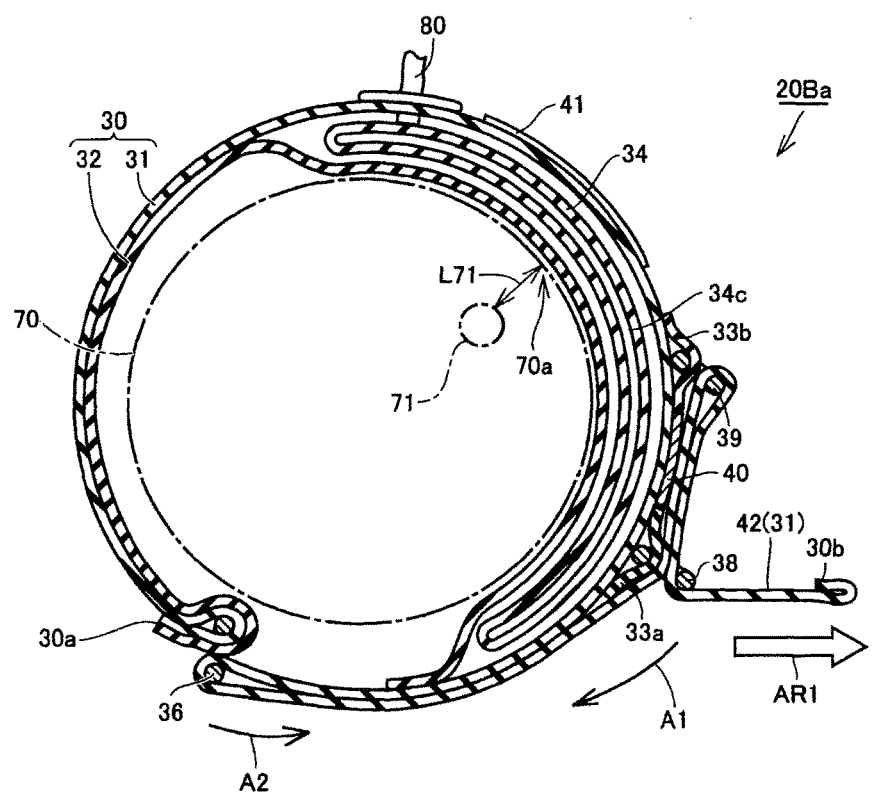
FIG. 13 is a cross-sectional view illustrating a cuff according to a variation on the second embodiment.

As shown in FIG. 13, the difference between the second embodiment and the present variation lies in the other end portion 30b that is passed through the third loop-shaped ring 39 being passed through the second loop-shaped ring 38 once again after being bent back in the third loop-shaped ring 39. The other end portion 30b is passed through the insertion hole of the second loop-shaped ring 38, and is led out toward the outer side from the portion of the outer cover 30 that is formed in the circular shape.

Figure 14:
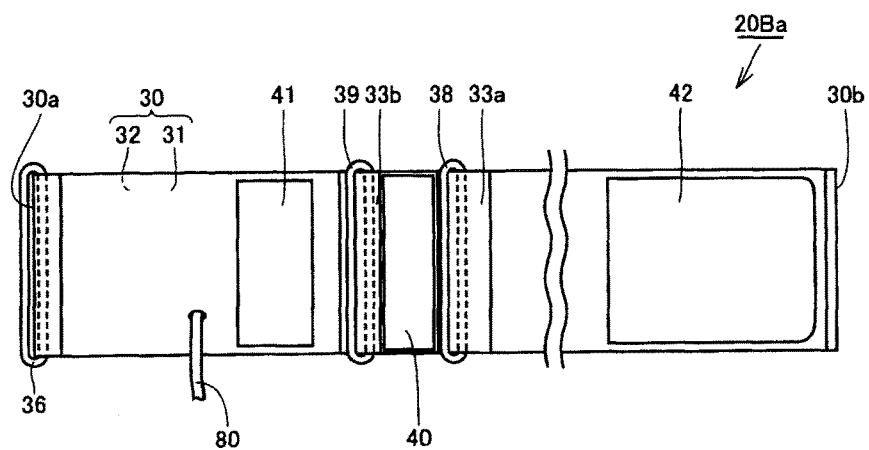
FIG. 14 is a plan view illustrating the cuff according to the variation on the second embodiment in an unrolled state.

As shown in FIG. 14, as with the cuff 20B according to the aforementioned second embodiment, the third loop-shaped ring 39 is located between the first loop-shaped ring 36 and the second loop-shaped ring 38 in the lengthwise direction of the outer cover 30 when the outer cover 30 is in an unrolled state.

Actions and Effects

With the cuff 20Ba according to the present variation, the left upper arm 70, for example, of the measurement subject is inserted into the portion of the outer cover 30 that is formed into a circular shape. After the upper arm has been inserted, the other end portion 30b of the outer cover 30 is gripped by the right hand (not shown). The gripped other end portion 30b is then pulled in the direction indicated by the arrow AR1.

When the other end portion 30b is pulled in the direction indicated by the arrow AR1, the second loop-shaped ring 38 is also pulled in the direction indicated by the arrow AR1 by the other end portion 30b side of the outer cover 30.

In order to achieve a desired tightened state for the cuff 20Ba, the other end portion 30b of the outer cover 30 is pulled by the right hand in the direction indicated by the arrow AR1. The diameter of the portion of the outer cover 30 formed into a circular shape gradually decreases.

The portion of the outer cover 30 on the side where the second loop-shaped ring 38 and the third loop-shaped ring 39 are provided (what is essentially the right half of the outer cover 30 in the drawings) is pulled toward the first loop-shaped ring 36, and attempts to rotate in the direction indicated by the arrow A1 (the clockwise direction).

Here, as described above, a force that attempts to move the second loop-shaped ring 38 in the direction indicated by the arrow AR1 also acts on the second loop-shaped ring 38. This force acts so as to continually position the second loop-shaped ring 38 on the rightmost side of the upper arm 70. This force works reactively against the force that attempts to rotate the second loop-shaped ring 38 and the third loop-shaped ring 39 in the direction indicated by the arrow A1 (the clockwise direction).

In other words, two forces act on the second loop-shaped ring 38 and the third loop-shaped ring 39: the force that attempts to rotate the rings in the clockwise direction, and the force that works in the counter-clockwise direction reactively against that force. These forces cancel each other out, and thus the positions of the second loop-shaped ring 38 and the third loop-shaped ring 39 in the circumferential direction relative to the upper arm 70 experience almost no change.

Accordingly, the first loop-shaped ring 36 is gradually pulled in the direction indicated by the arrow A2. The diameter of the portion of the outer cover 30 formed into a circular shape gradually decreases. The diameter of the portion of the outer cover 30 that is formed in a circular shape can be reduced with the position of the second loop-shaped ring 38 and the third loop-shaped ring 39 in the circumferential direction relative to the upper arm 70 experiencing almost no change.

After the other end portion 30b that has been passed through the third loop-shaped ring 39 is bent back in the third loop-shaped ring 39, the other end portion 30b is again passed through the second loop-shaped ring 38. The outer cover 30 is doubly passed through the second loop-shaped ring 38 and is bent back in the third loop-shaped ring 39. According to this configuration, the outer cover 30 can be held in a secured state against the upper arm 70 even if an engagement means such as a surface fastener is not used.

Note that a so-called curler-shaped resilient member 40 may be provided between the second loop-shaped ring 38 and the third loop-shaped ring 39 in the lengthwise direction of the outer cover 30 when the outer cover 30 is in an unrolled state. The resilient member 40 is anchored to an area of the outer cover 30 that is positioned between the second loop-shaped ring 38 and the third loop-shaped ring 39. The resilient member 40 may be covered by an anchoring cover (not shown) or the like. The resilient member 40 maintains a constant space between the second loop-shaped ring 38 and the third loop-shaped ring 39. By providing the resilient member 40, the outer cover 30 can be secured to the upper arm 70 with ease.

Third Embodiment

A sphygmomanometer according to a third embodiment will be described with reference to FIGS. 15 and 16. Here, only the differences from the second embodiment will be described. The difference between the second embodiment and the present embodiment lies in the location where the third loop-shaped ring 39 is attached.

Figure 16:
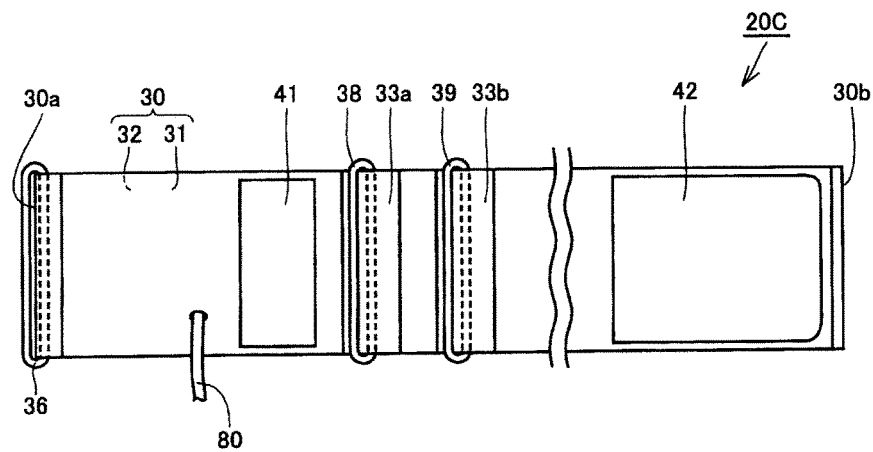
FIG. 16 is a plan view illustrating the cuff according to the third embodiment in an unrolled state.

As shown in FIG. 16, the third loop-shaped ring 39 is located between the second loop-shaped ring 38 and the other end portion 30b of the outer cover 30 in the lengthwise direction of the outer cover 30 when the outer cover 30 is in an unrolled state.

Figure 15:
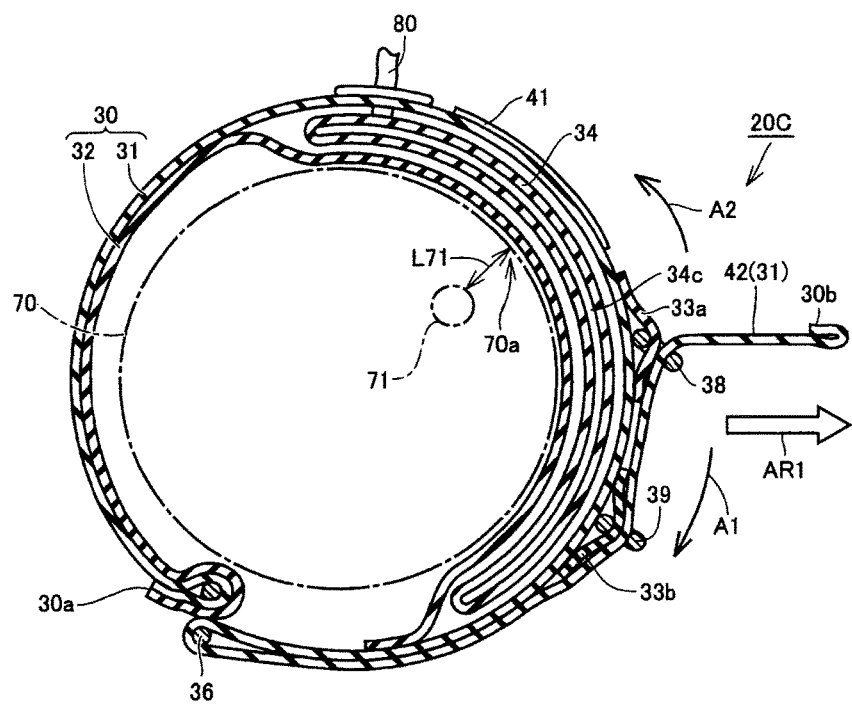
FIG. 15 is a cross-sectional view illustrating a cuff according to a third embodiment.

As shown in FIG. 15, the other end portion 30b of the outer cover 30 that has been passed through the first loop-shaped ring 36 is overlaid along the outer side (the front surface 31 side) of the portion of the outer cover 30 that is formed into a circular shape. The other end portion 30b is passed through the insertion hole of the third loop-shaped ring 39.

The other end portion 30b of the outer cover 30 that has been inserted into the insertion hole of the third loop-shaped ring 39 is overlaid along the outer side (the front surface 31 side) of the portion of the outer cover 30 that is formed in the circular shape. The other end portion 30b is inserted into the insertion hole 38a of the second loop-shaped ring 38, and is led out toward the outer side from the portion of the outer cover 30 that is formed in the circular shape.

Actions and Effects

With the cuff 20C, the left upper arm 70, for example, of the measurement subject is inserted into the portion of the outer cover 30 that is formed into a circular shape. After the upper arm 70 has been inserted, the other end portion 30b of the outer cover 30 is gripped by the right hand (not shown). The gripped other end portion 30b is then pulled in the direction indicated by the arrow AR1.

When the other end portion 30b is pulled in the direction indicated by the arrow AR1, the second loop-shaped ring 38 is also pulled in the direction indicated by the arrow AR1 by the other end portion 30b side of the outer cover 30.

In order to achieve a desired tightened state for the cuff 20C, the other end portion 30b of the outer cover 30 is pulled further by the right hand in the direction indicated by the arrow AR1. The diameter of the portion of the outer cover 30 formed into a circular shape gradually decreases.

The portion of the outer cover 30 on the side where the second loop-shaped ring 38 and the third loop-shaped ring 39 are provided (what is essentially the right half of the outer cover 30 in the drawings) is pulled toward the first loop-shaped ring 36, and attempts to rotate in the direction indicated by the arrow A1 (the clockwise direction).

A force that attempts to rotate the second loop-shaped ring 38 in the direction indicated by the arrow A1 (the clockwise direction) acts on the second loop-shaped ring 38.

Here, as described above, a force that attempts to move the second loop-shaped ring 38 in the direction indicated by the arrow AR1 also acts on the second loop-shaped ring 38. This force acts so as to continually position the second loop-shaped ring 38 on the rightmost side of the upper arm 70. This force works reactively in the direction indicated by an arrow A2 (the counter-clockwise direction), against the force that attempts to rotate the second loop-shaped ring 38 in the direction indicated by the arrow A1 (the clockwise direction).

In other words, two forces act on the second loop-shaped ring 38: the force that attempts to rotate the second loop-shaped ring 38 in the clockwise direction, and the force that works reactively against that force. These forces cancel each other out, and thus the position of the second loop-shaped ring 38 in the circumferential direction relative to the upper arm 70 experiences almost no change. Accordingly, the diameter of the portion of the outer cover 30 that is formed in a circular shape can be reduced with the position of the second loop-shaped ring 38 in the circumferential direction relative to the upper arm 70 experiencing almost no change.

The outer cover 30 and the upper arm 70 come into tight contact with each other, thus completing the securing of the cuff 20C to the upper arm 70.

Here, the third loop-shaped ring 39 is located between the second loop-shaped ring 38 and the other end portion 30b of the outer cover 30 in the lengthwise direction of the outer cover 30 when the outer cover 30 is in an unrolled state. The portion of the outer cover 30 in which the attachment cover 33a is provided is continuous with the portion of the outer cover 30 that contains the air bladder 34. As a result, the second loop-shaped ring 38 and the air bladder 34 move relationally (that is, in tandem) in the circumferential direction.

As described above, the position of the second loop-shaped ring 38 relative to the upper arm 70 experiences almost no change between before and after the outer cover 30 is secured to the upper arm 70. Therefore, the position of the air bladder 34 relative to the upper arm 70 also experiences almost no change between before and after the outer cover 30 is secured to the upper arm 70.

As described initially, the rotation in the circumferential direction and the rotation in the opposite direction as that rotation are not repeated before and after the sphygmomanometer cuff 20C is secured. Even if the cuff 20C is secured to the upper arm 70 on a daily basis, the second loop-shaped ring 38 is, by design, repeatedly disposed in approximately the same position near the rightmost side of the upper arm 70. The air bladder 34 can also, by design, be repeatedly disposed in approximately the same position, which makes it possible to repeatedly recreate a predetermined tightened state for the cuff 20C.

According to the cuff 20C and a sphygmomanometer provided therewith, the occurrence of measurement errors caused by shifts in the fitting position is reduced, which makes it possible to measure the blood pressure information in an accurate and stable manner without variations occurring in the measured values.

Fourth Embodiment

A sphygmomanometer according to a fourth embodiment will be described with reference to FIGS. 17 and 18. Here, only the differences from the second embodiment will be described. The difference between the second embodiment and the present embodiment lies in the location where the third loop-shaped ring 39 is attached.

Figure 18:
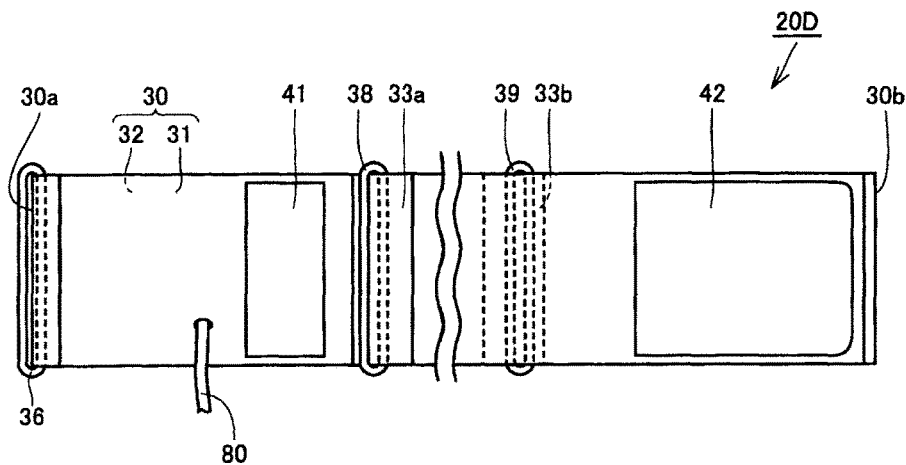
FIG. 18 is a plan view illustrating the cuff according to the fourth embodiment in an unrolled state.

As shown in FIG. 18, the third loop-shaped ring 39 is provided on the rear surface 32 of the outer cover 30. The third loop-shaped ring 39 is located between the second loop-shaped ring 38 and the other end portion 30b of the outer cover 30 in the lengthwise direction of the outer cover 30 when the outer cover 30 is in an unrolled state.

Figure 17:
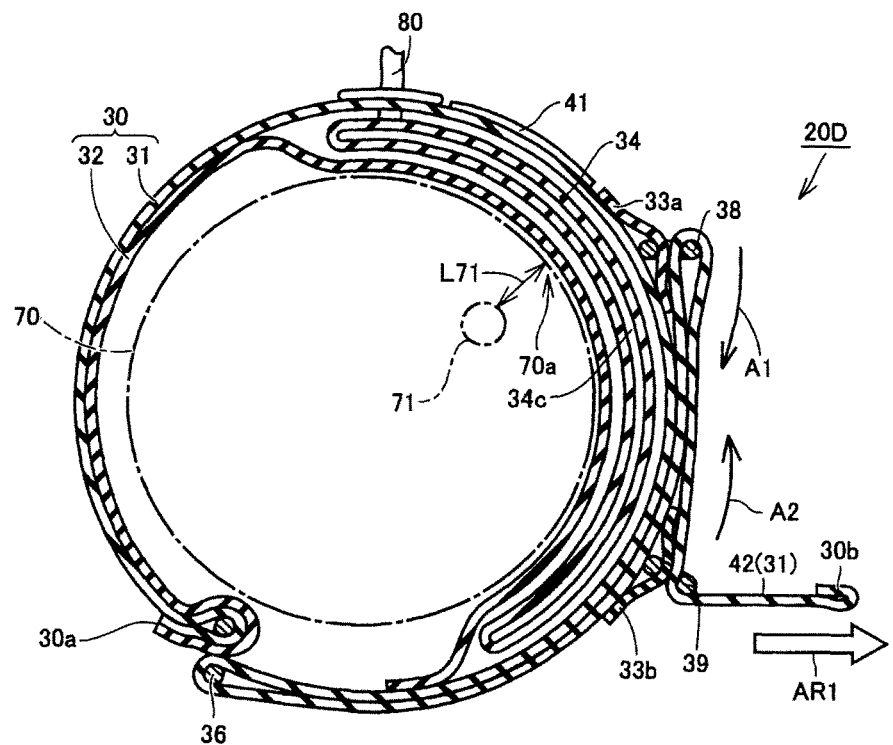
FIG. 17 is a cross-sectional view illustrating a cuff according to a fourth embodiment.

As shown in FIG. 17, the other end portion 30b of the outer cover 30 that has been passed through the first loop-shaped ring 36 is overlaid along the outer side (the front surface 31 side) of the portion of the outer cover 30 that is formed into a circular shape. The other end portion 30b is passed through the insertion hole 38a of the second loop-shaped ring 38 and bent back.

The other end portion 30b of the outer cover 30 that has been passed through the second loop-shaped ring 38 and bent back is overlaid along the outer side (the rear surface 32 side) of the portion of the outer cover 30 that is formed in the circular shape. The other end portion 30b is passed through the insertion hole of the third loop-shaped ring 39, and is led out toward the outer side from the portion of the outer cover 30 that is formed in the circular shape.

Actions and Effects

With the cuff 20D, the left upper arm 70, for example, of the measurement subject is inserted into the portion of the outer cover 30 that is formed into a circular shape. After the upper arm 70 has been inserted, the other end portion 30b of the outer cover 30 is gripped by the right hand (not shown). The gripped other end portion 30b is then pulled in the direction indicated by the arrow AR1.

When the other end portion 30b is pulled in the direction indicated by the arrow AR1, the third loop-shaped ring 39 is also pulled in the direction indicated by the arrow AR1 by the other end portion 30b side of the outer cover 30.

The portion of the outer cover 30 in which the third loop-shaped ring 39 is provided is pulled toward the second loop-shaped ring 38 and rotates in the direction indicated by the arrow A2 (the counter-clockwise direction). The portion of the outer cover 30 in which the second loop-shaped ring 38 is provided is pulled toward the third loop-shaped ring 39 and rotates in the direction indicated by the arrow A1 (the clockwise direction).

In order to achieve a desired tightened state for the cuff 20D, the other end portion 30b of the outer cover 30 is pulled by the right hand in the direction indicated by the arrow AR1. The diameter of the portion of the outer cover 30 formed into a circular shape gradually decreases.

The second loop-shaped ring 38 and the third loop-shaped ring 39 approach each other. The second loop-shaped ring 38 and the third loop-shaped ring 39 then become adjacent to each other in the circumferential direction, essentially functioning as a single entity.

When the other end portion 30b is pulled in the direction indicated by the arrow AR1, the second loop-shaped ring 38 and the third loop-shaped ring 39 are also pulled in the direction indicated by the arrow AR1 by the other end portion 30b side of the outer cover 30, while functioning essentially as a single entity.

At the same time, the portion of the outer cover 30 on the side where the second loop-shaped ring 38 and the third loop-shaped ring 39 are provided (what is essentially the right half of the outer cover 30 in the drawings) is pulled toward the first loop-shaped ring 36, and attempts to rotate in the direction indicated by the arrow A1 (the clockwise direction). A force that attempts to rotate the second loop-shaped ring 38 and the third loop-shaped ring 39 in the direction indicated by the arrow A1 (the clockwise direction) acts on the second loop-shaped ring 38 and the third loop-shaped ring 39.

Here, as described above, a force that attempts to move the second loop-shaped ring 38 and the third loop-shaped ring 39 in the direction indicated by the arrow AR1 also acts on the second loop-shaped ring 38 and the third loop-shaped ring 39. This force acts so as to continually position the second loop-shaped ring 38 and the third loop-shaped ring 39 on the rightmost side of the upper arm 70. This force works reactively in the direction indicated by the arrow A2 (the counter-clockwise direction), against the force that attempts to rotate the second loop-shaped ring 38 and the third loop-shaped ring 39 in the direction indicated by the arrow A1 (the clockwise direction).

In other words, two forces act on the second loop-shaped ring 38 and the third loop-shaped ring 39: the force that attempts to rotate the second loop-shaped ring 38 and the third loop-shaped ring 39 in the clockwise direction, and the force that works reactively against that force. These forces cancel each other out, and thus the positions of the second loop-shaped ring 38 and the third loop-shaped ring 39 in the circumferential direction relative to the upper arm 70 experience almost no change.

Accordingly, after the second loop-shaped ring 38 and the third loop-shaped ring 39 have become adjacent to each other, the diameter of the portion of the outer cover 30 that is formed into a circular shape can be reduced with the position of the second loop-shaped ring 38 and the third loop-shaped ring 39 in the circumferential direction relative to the upper arm 70 experiencing almost no change.

Here, the second loop-shaped ring 38 is provided on the front surface 31 of the outer cover 30. The portion of the outer cover 30 in which the attachment cover 33a is provided is continuous with the portion of the outer cover 30 that contains the air bladder 34. As a result, the second loop-shaped ring 38 and the air bladder 34 move relationally (that is, in tandem) in the circumferential direction.

As described above, from before the outer cover 30 is secured to the upper arm 70 to after the outer cover 30 is secured to the upper arm 70, the second loop-shaped ring 38 moves in the clockwise direction (the direction indicated by the arrow A1) by a predetermined distance until the second loop-shaped ring 38 becomes adjacent to the third loop-shaped ring 39. As a result, from before the outer cover 30 is secured to the upper arm 70 to after the outer cover 30 is secured to the upper arm 70, the position of the air bladder 34 relative to the upper arm 70 also moves in the clockwise direction (the direction indicated by the arrow A1) by a predetermined distance.

With the sphygmomanometer cuff 20D according to the present embodiment, although the air bladder 34 moves in the clockwise direction by a predetermined distance, the rotation in the circumferential direction and the rotation in the direction opposite to that rotation are not repeated during the process of securing the cuff 20D, as described initially. Even if the cuff 20D is secured to the upper arm 70 on a daily basis, the third loop-shaped ring 39 is, by design, repeatedly disposed in approximately the same position near the rightmost side of the upper arm 70.

As a result, although the air bladder 34 moves in the clockwise direction by a predetermined distance, the position of the air bladder 34 is, by design, repeatedly disposed in approximately the same position, and thus, it is possible to repeatedly recreate a predetermined tightened state for the cuff 20D.

According to the cuff 20D and a sphygmomanometer provided therewith, the occurrence of measurement errors caused by shifts in the fitting position is reduced, which makes it possible to measure the blood pressure information in an accurate and stable manner without variations occurring in the measured values.

Comparative Example

Figure 19:
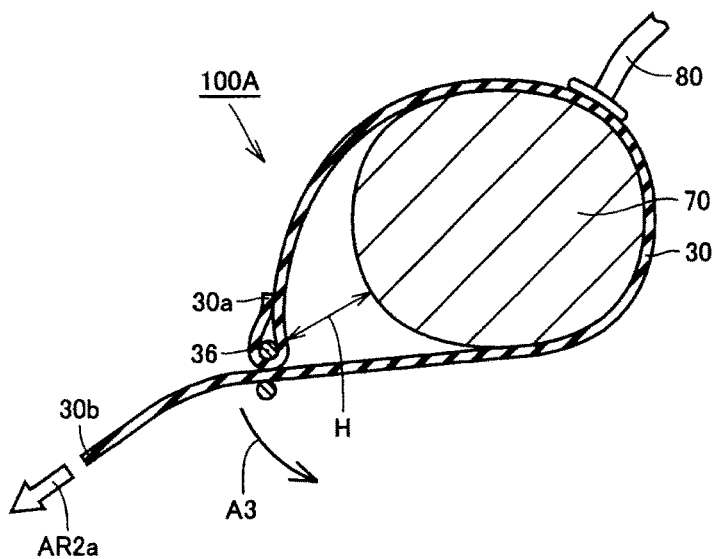
FIG. 19 is a first cross-sectional view illustrating, over time, the fitting of a cuff according to a comparative example onto an upper arm.
Figure 20:
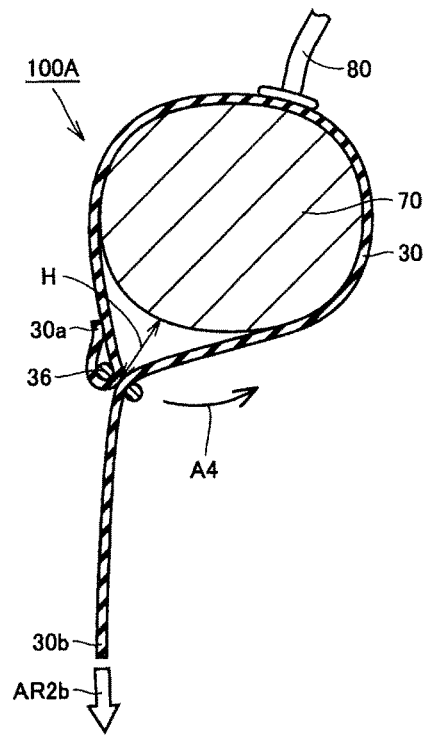
FIG. 20 is a second cross-sectional view illustrating, over time, the fitting of a cuff according to the comparative example onto an upper arm.
Figure 21:
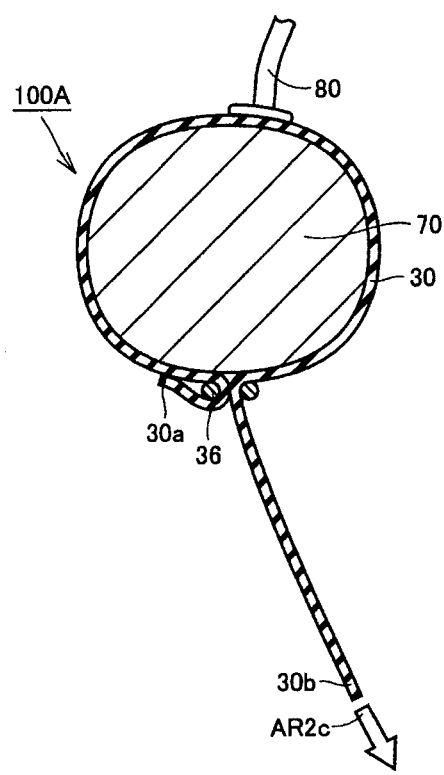
FIG. 21 is a third cross-sectional view illustrating, over time, the fitting of a cuff according to the comparative example onto an upper arm.

The securing of a cuff 100A according to a comparative example to the upper arm 70 will be described with reference to FIGS. 19 through 21. The cuff 100A according to the comparative example differs from the aforementioned first through fourth embodiments in that only the first loop-shaped ring 36 is provided as a guide member. In FIGS. 19 through 21, the air bladder 34 is not shown.

FIGS. 19 through 21 are cross-sectional views illustrating, over time, the fitting (process of fitting) of the cuff 100A according to the comparative example to the upper arm 70. The state shown in FIG. 19 transitions to the state shown in FIG. 20, and then progresses to the state shown in FIG. 21. The configuration of the cuff 100A according to the present comparative example is essentially the same as the configuration disclosed in JP H5-39504U (Patent Literature 1).

As shown in FIG. 19, with the cuff 100A, the left upper arm 70, for example, of the measurement subject is inserted into the portion of the outer cover 30 that is formed into a circular shape.

After the upper arm 70 has been inserted into the portion of the outer cover 30 that has been formed into a circular shape, the other end portion 30b of the outer cover 30 is gripped by the right hand. The other end portion 30b of the outer cover 30 is pulled by the right hand in the direction indicated by an arrow AR2a.

The first loop-shaped ring 36 is pulled in the direction indicated by the arrow AR2a by the other end portion 30b side of the outer cover 30. The gap H is formed between the upper arm 70 and the outer cover 30 on the side on which the first loop-shaped ring 36 is provided.

In order to achieve a desired tightened state for the cuff 100A, the other end portion 30b of the outer cover 30 is pulled by the right hand in the direction indicated by the arrow AR2a. The diameter of the portion of the outer cover 30 formed into a circular shape gradually decreases, and the gap H also decreases as a result.

When the gap H decreases, at the area where the outer cover 30 and the upper arm 70 make contact, the side of the outer cover 30 that is to be passed through the first loop-shaped ring 36 attempts to slide along the surface of the upper arm 70 while making contact with the upper arm 70.

However, a large amount of friction is produced between the outer cover 30 and the upper arm 70, and thus the outer cover 30 for the most part cannot slide along the surface of the upper arm 70. Due to this friction, the direction in which the other end portion 30b of the outer cover 30 is pulled by the right hand rotates to the direction indicated by an arrow A3.

As shown in FIG. 20, the force acting in the direction indicated by the arrow AR2a (see FIG. 19) changes to the direction indicated by an arrow AR2b (see FIG. 20). When the direction in which the other end portion 30b of the outer cover 30 is being pulled changes to the direction indicated by the arrow AR2b, the outer cover 30 also rotates in the direction indicated by the arrow AR2b (the counter-clockwise direction). At this time, there are cases where the measurement subject rotates the outer cover 30 in the clockwise direction in order to return the outer cover 30, which has rotated in the counter-clockwise direction, to its original position.

In order to achieve a desired tightened state for the cuff 100A, the other end portion 30b of the outer cover 30 is pulled by the right hand in the direction indicated by the arrow AR2b. The diameter of the portion of the outer cover 30 formed into a circular shape gradually decreases, and the gap H also decreases as a result.

However, a large amount of friction is produced between the outer cover 30 and the upper arm 70, and thus the outer cover 30 for the most part cannot slide along the surface of the upper arm 70. Due to this friction, the direction in which the other end portion 30b of the outer cover 30 is pulled by the right hand rotates to the direction indicated by an arrow A4.

As shown in FIG. 21, the force acting in the direction indicated by the arrow AR2b (see FIG. 20) further changes to the direction indicated by an arrow AR2c (see FIG. 21). When the direction in which the other end portion 30b of the outer cover 30 is being pulled changes to the direction indicated by the arrow AR2c, the outer cover 30 rotates in the direction indicated by the arrow A4 (see FIG. 20; the counter-clockwise direction). At this time, there are cases where the measurement subject further rotates the outer cover 30 in the clockwise direction in order to return the outer cover 30, which has rotated in the counter-clockwise direction, to its original position.

Ultimately, the outer cover 30 and the upper arm 70 come into tight contact with each other, and thus the gap H is essentially eliminated. This completes the securing of the cuff 100A to the upper arm 70.

The cuff 100A according to the present comparative example is fitted to the measurement area by repeating rotation in the circumferential direction and rotation in the direction opposite to the circumferential direction multiple times. According to the cuff 100A, in the case where a blood pressure value is, for example, measured on a daily basis, it is difficult to recreate the predetermined tightened state for the cuff. As a result, variations appear in the measured values obtained through the day-to-day measurements, which makes it difficult to measure the blood pressure information in an accurate and stable manner.

As opposed to this, with the cuffs (20A through 20D) and sphygmomanometers provided therewith according to the aforementioned first through fourth embodiments, a predetermined tightened state can be repeatedly recreated. Thus the occurrence of measurement errors caused by shifts in the fitting position is reduced, which makes it possible to measure the blood pressure information in an accurate and stable manner without variations occurring in the measured values.

Although the first through fourth embodiments describe, as an example, a so-called upper arm-type sphygmomanometer in which the cuff is affixed to the upper arm when measuring a blood pressure value, and a sphygmomanometer cuff provided therein, one or more embodiments of the present invention are not particularly limited thereto.

It is also possible to apply the configurations of the first through fourth embodiments in a so-called wrist-type sphygmomanometer in which the cuff is affixed to the wrist when measuring a blood pressure value, and a sphygmomanometer cuff provided therein.

The configurations of the first through fourth embodiments can also be applied in a so-called ankle-type sphygmomanometer in which the cuff is affixed to the ankle when measuring a blood pressure value, and a sphygmomanometer cuff provided therein.

Although the first through fourth embodiments describe examples in which the configurations are applied in a sphygmomanometer capable of measuring a systolic blood pressure value, a diastolic blood pressure value, and so on, and in a sphygmomanometer cuff provided therein, one or more embodiments of the present invention are not particularly limited thereto.

The configurations of the first through fourth embodiments can also be applied in a blood pressure information measurement device capable of measuring other blood pressure information aside from blood pressure values such as a systolic blood pressure value and a diastolic blood pressure value (for example, an average blood pressure value, a sphygmogram, a pulse, an AI (augmentation index) value, and so on), and in a blood pressure information measurement device cuff provided therein.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1 sphygmomanometer
10 main body
11 control unit
12 display unit
13 memory unit
13a processing memory
13b data memory
14 power source unit
15 operating unit
15a power switch
15b measurement switch
15c stop switch
15d record call switch
16 air system component
16a pressure pump
16b exhaust valve
16c pressure sensor
17a pressure pump driving circuit
17b exhaust valve driving circuit
17c oscillation circuit 20, 20A, 20Aa, 20Ab, 20Ac, 20B, 20Ba, 20C, 20D, 100A cuff
30 outer cover
30a one end portion
30b other end portion
31 front surface
32 rear surface
33a, 33b attachment cover
34 air bladder
34c position
36 first loop-shaped ring
36a, 38a insertion hole
38 second loop-shaped ring
39 third loop-shaped ring
40 anchoring member
41, 42 surface fastener
50, 50a anchoring member
52 support frame
52a side wall portion
52a1, 52b1 shaft support hole
54 first roller
56 second roller
70 upper arm
70a, R area
71 artery
72 upper arm triceps
80 air tube
A1 through A4, AR1, AR1a, AR2a, AR2b, AR2c, AR54, AR56 arrow
L71 distance
H gap
ST1 through ST13 step

The invention claimed is:

1. A blood pressure information measurement device cuff comprising:
a fluid bladder that is configured to apply pressure to a body;
a band-shaped outer cover, comprising a first main surface and a second main surface that is configured to oppose the body by being wrapped around the body in a circular shape, that contains the fluid bladder, said band-shaped outer cover having a holding portion that holds the fluid bladder; a first end portion; and a second end portion, wherein the first end portion is located closer to the holding portion than the second end portion, the band-shaped outer cover further comprising an attachment cover attached to the first main surface;
a first ring-shaped guide member having a first ring portion and a second ring portion, the first ring portion of the first ring-shaped guide member being firmly connected to the first end portion of the band-shaped outer cover; and
a second ring-shaped guide member having a first ring portion and a second ring portion, the second ring-shaped guide member being attached to the first main surface of the band-shaped outer cover by being sandwiched between the attachment cover and the band-shaped outer cover,
wherein the second end portion of the band-shaped outer cover is configured to pass through the first ring-shaped guide member and to be bent back slidably at the second ring portion of the first ring-shaped guide member, and further to pass through the second ring-shaped guide member at the second ring portion of the second ring-shaped guide member, and wherein a portion of the band-shaped outer cover on a side where the second ring-shaped guide member is provided is configured to be pulled toward the first ring-shaped guide member, causing a clockwise force and a counter-clockwise force to act on the second ring portion of the second ring-shaped guide member.

2. The blood pressure information measurement device cuff according to claim 1, wherein the outer cover is configured to be anchored to the body in a state in which an area of the surface of the body where a distance to an artery within the body is the shortest and the fluid bladder are disposed opposite to each other.

3. The blood pressure information measurement device cuff according to claim 1,
wherein the body is an upper arm, and
wherein the second ring-shaped guide member is provided on the first main surface that is configured to be located toward a triceps of the upper arm during use of the blood pressure information measurement device cuff, which is configured to be anchored to the upper arm.

4. The blood pressure information measurement device cuff according to claim 1,
wherein the body is a first upper arm of a measurement subject, and
wherein the second ring-shaped guide member is provided on the first main surface that is configured to be located toward a second upper arm of the measurement subject during use of the blood pressure information measurement device cuff, which is configured to be anchored to the first upper arm.

5. The blood pressure information measurement device cuff according to claim 1, further comprising:
a fastening member provided on the first main surface,
wherein the fastening member is located between the second ring-shaped guide member and the first ring-shaped guide member, and closer to the second ring-shaped guide member, in the lengthwise direction of the outer cover when the outer cover is in an unrolled state.

6. The blood pressure information measurement device cuff according to claim 1, further comprising:
a third ring-shaped guide member, provided on the first main surface, that is located between the first ring-shaped guide member and the second ring-shaped guide member in the lengthwise direction of the outer cover when the outer cover is in an unrolled state,
wherein the second end portion that has been passed through the second ring-shaped guide member is passed through the third ring-shaped guide member.

7. The blood pressure information measurement device cuff according to claim 6, wherein the second end portion that has been passed through the third ring-shaped guide member is bent back in the third ring-shaped guide member and is then once again passed through the second ring-shaped guide member.

8. The blood pressure information measurement device cuff according to claim 1, further comprising:
a third ring-shaped guide member, provided on the first main surface, that is located between the second ring-shaped guide member and the another second end portion in the lengthwise direction of the outer cover when the outer cover is in an unrolled state,
wherein the another second end portion that has been passed through the first ring-shaped guide member and bent back is passed through the second ring-shaped guide member after being passed through the third ring-shaped guide member.

9. The blood pressure information measurement device cuff according to claim 1, further comprising:
a third ring-shaped guide member, provided on the second main surface, that is located between the second ring-shaped guide member and the another second end portion in the lengthwise direction of the outer cover when the outer cover is in an unrolled state,
wherein the another second end portion that has been passed through the second ring-shaped guide member is passed through the third ring-shaped guide member after being bent back in the second ring-shaped guide member.

10. A blood pressure information measurement device comprising:
the blood pressure information measurement device cuff according to claim 1;
an inflation/deflation mechanism that inflates/deflates the fluid bladder; and
a blood pressure information obtainment unit that obtains blood pressure information.

\* \* \* \* \*